US012788299B2

(12) United States Patent
Farmer et al.

(10) Patent No.: US 12,788,299 B2
(45) Date of Patent: Nov. 10, 2026

(54) METHOD AND APPARATUS FOR PERFORMING ELECTRORETINOGRAPHY, INCLUDING ENHANCED ELECTRODE

(71) Applicant: Diagnosys LLC, Lowell, MA (US)

(72) Inventors: Jeffrey D. Farmer, Chelmsford, MA (US); Bruce Doran, Westford, MA (US); Richard Robson, Holt (GB)

(73) Assignee: Diagnosys LLC, Lowell, MA (US)

( * ) Notice: Subject to any disclaimer, the term of this patent is extended or adjusted under 35 U.S.C. 154(b) by 934 days.

(21) Appl. No.: 17/688,285

(22) Filed: Mar. 7, 2022

(65) Prior Publication Data

US 2022/0280097 A1 Sep. 8, 2022

Related U.S. Application Data

(60) Provisional application No. 63/157,272, filed on Mar. 5, 2021.

(51) Int. Cl.
*A61B 5/297* (2021.01)
*A61B 5/257* (2021.01)
(Continued)

(52) U.S. Cl.
CPC .............. *A61B 5/297* (2021.01); *A61B 5/257* (2021.01); *A61B 5/268* (2021.01); *A61B 5/27* (2021.01);
(Continued)

(58) Field of Classification Search
CPC ....... A61B 5/273; A61B 5/315; A61B 5/6821; A61B 2562/12; A61B 2562/125
See application file for complete search history.

(56) References Cited

U.S. PATENT DOCUMENTS

| | | | |
|---|---|---|---|
| 3,001,441 | A | 9/1961 | Herbert |
| 3,012,472 | A | 12/1961 | Feinberg et al. |

(Continued)

FOREIGN PATENT DOCUMENTS

| | | |
|---|---|---|
| CN | 101019760 | 8/2017 |
| CN | 107582053 | 1/2018 |

(Continued)

OTHER PUBLICATIONS

Woo J., Jung, S., Gauvin, M., Lachapelle, P. The DTL ERG electrode comes in different shapes and sizes: Are they all good?, Jul. 24, 2017, Doc Ophthalmol, 135:155-164. (Year: 2017).*

(Continued)

*Primary Examiner* — Eun Hwa Kim
(74) *Attorney, Agent, or Firm* — Pandiscio & Pandiscio

(57) ABSTRACT

Apparatus for use in performing electroretinography on a test subject, the apparatus comprising: at least one electrically conductive thread, the at least one electrically conductive thread comprising a first end and a second end, wherein the first end of the at least one electrically conductive thread is configured to mount to skin on one side of an eye of the test subject and the second end is configured to mount to skin on the opposite side of the eye of the test subject, such that the at least one electrically conductive thread is in contact with a surface film of an eye; and an electrically non-conductive coating applied to at least one region of the at least one electrically conductive thread, whereby to electrically isolate the at least one region of the at least one electrically conductive thread from the eye.

31 Claims, 15 Drawing Sheets

(51) Int. Cl.

| | |
|---|---|
| ***A61B 5/268*** | (2021.01) |
| ***A61B 5/27*** | (2021.01) |
| ***A61B 5/273*** | (2021.01) |
| ***A61B 5/398*** | (2021.01) |
| ***G01N 27/30*** | (2006.01) |

(52) U.S. Cl.

CPC .............. *A61B 5/273* (2021.01); *A61B 5/398* (2021.01); *G01N 27/30* (2013.01); *A61B 2562/043* (2013.01); *A61B 2562/14* (2013.01); *A61B 2562/222* (2013.01)

(56) References Cited

U.S. PATENT DOCUMENTS

| | | | |
|---|---|---|---|
| 3,439,157 | A | 4/1969 | Myles |
| 4,131,113 | A | 12/1978 | Fender et al. |
| 4,362,164 | A | 12/1982 | Little et al. |
| 4,417,581 | A | 11/1983 | Dawson |
| 4,618,230 | A | 10/1986 | Ens et al. |
| 4,740,072 | A | 4/1988 | Griffin et al. |
| 4,806,289 | A | 2/1989 | Laursen et al. |
| 4,874,237 | A | 10/1989 | Cringle |
| 4,895,169 | A | 1/1990 | Heath |
| 4,910,090 | A | 3/1990 | Kuhlman et al. |
| 4,913,160 | A | 4/1990 | John |
| 4,961,423 | A | 10/1990 | Canducci |
| 5,141,305 | A | 8/1992 | Young |
| 5,154,174 | A | 10/1992 | Hawlina |
| 5,767,450 | A | 6/1998 | Furruhata |
| 5,943,110 | A | 8/1999 | Yoda et al. |
| 5,943,116 | A | 8/1999 | Zeimer |
| 6,231,187 | B1 | 5/2001 | Munoz et al. |
| 6,419,638 | B1 | 7/2002 | Hay et al. |
| 7,787,959 | B1 | 8/2010 | Morgan |
| 8,810,482 | B2 | 8/2014 | Abdollahi et al. |
| 9,026,189 | B2 | 5/2015 | Garcia et al. |
| 10,820,824 | B2 | 11/2020 | Doran et al. |
| 10,893,823 | B2 | 1/2021 | Doran et al. |
| 11,357,442 | B2 | 6/2022 | Doran et al. |
| 2003/0020875 | A1 | 1/2003 | Sperling |
| 2003/0149350 | A1 | 8/2003 | Porciatti |
| 2004/0057013 | A1 | 3/2004 | Cappo et al. |
| 2005/0119544 | A1 | 6/2005 | Valjakka et al. |
| 2005/0245796 | A1 | 11/2005 | Woods et al. |
| 2006/0058857 | A1 | 3/2006 | Tano et al. |
| 2006/0095108 | A1 | 5/2006 | Chowdhury et al. |
| 2006/0184062 | A1 | 8/2006 | Greenberg et al. |
| 2006/0244915 | A1 | 11/2006 | Clemons et al. |
| 2008/0294066 | A1 | 11/2008 | Hetling et al. |
| 2009/0018419 | A1 | 1/2009 | Torch |
| 2010/0091242 | A1 | 4/2010 | Baglini et al. |
| 2010/0249532 | A1 | 9/2010 | Maddess et al. |
| 2010/0292999 | A1 | 11/2010 | Verma |
| 2011/0118584 | A1 | 5/2011 | Gratteau |
| 2011/0170064 | A1 | 7/2011 | Taylor |
| 2012/0069296 | A1 | 3/2012 | Li et al. |
| 2012/0143080 | A1 | 6/2012 | Greenburg et al. |
| 2013/0066396 | A1 * | 3/2013 | Gekeler ............. A61N 1/36046 607/53 |
| 2013/0242077 | A1 | 9/2013 | Lin et al. |
| 2013/0278899 | A1 | 10/2013 | Waldorf et al. |
| 2013/0285886 | A1 | 10/2013 | Pombo et al. |
| 2014/0128763 | A1 | 5/2014 | Fadem |
| 2014/0333898 | A1 | 11/2014 | Boate et al. |
| 2015/0029463 | A1 | 1/2015 | Hetling et al. |
| 2015/0191240 | A1 | 7/2015 | Burchard |
| 2015/0313467 | A1 | 11/2015 | Sakai et al. |
| 2017/0014074 | A1 | 1/2017 | Etzkorn et al. |
| 2017/0042441 | A1 | 2/2017 | Doran et al. |
| 2017/0127970 | A1 | 5/2017 | Doran et al. |
| 2018/0236230 | A1 | 8/2018 | Pilly |
| 2020/0129063 | A1 | 4/2020 | McGrath et al. |

FOREIGN PATENT DOCUMENTS

| | | |
|---|---|---|
| EP | 0225072 | 6/1987 |
| EP | 2314201 | 4/2011 |
| JP | 2011-087609 | 5/2011 |
| WO | WO 2001/078586 | 10/2001 |
| WO | WO 2005/002420 | 1/2005 |
| WO | WO 2008/024222 | 2/2008 |
| WO | WO 2008/070683 | 6/2008 |
| WO | WO 2010/066420 | 6/2010 |
| WO | WO 2015/191240 | 12/2015 |
| WO | WO 2016/162796 | 10/2016 |
| WO | WO2019/052239 | 3/2019 |
| WO | WO 2020/264263 | 12/2020 |
| WO | WO2021/044249 | 3/2021 |
| WO | WO2021/072073 | 4/2021 |

OTHER PUBLICATIONS

Berenzovsky, A. et al., Validation of a new fiber electrode prototype for clinical electroretinography, Arquivos Brasileiros de Oftalmologia, vol. 71, No. 3, Jun. 2008, pp. 316-320.

Burr-Brown Products From Texas Instruments, Single-Supply Differential Amplifier, Texas Instruments Incorporated, Jan. 2001.

Blanchard, P. et al., Using ESD Diodes as Voltage Clamps, Analog Dialogue 49-10, Oct. 2015, pp. 1-3.

ColorDome LabCradle: Advanced Animal ERG Testing, Diagnosys, LLC, Aug. 3, 2017.

EER Module: Electrically evoked response stimulator, Diagnosys LLC, Jul. 6, 2018.

Electrically Evoked Response: Note, Diagnosys, LLC, Jul. 6, 2018, pp. 1-8.

Frishman, Laura et al., ISCEV extended protocol for the photopic negative response (PhNR) of the full-field electroretinogram, Doc Ophthalmol, vol. 136, No. 3, May 31, 2018, pp. 207-211.

Heath, Janet, Amplifiers: What do rail-to-rail and single supply mean?, Analog IC Tips, 2017.

Luo, Xunda et al. Retinal Pathway Origins of the Pattern Electroretinogram (PERG), Investigative Ophthalmology & Visual Science, vol. 52, No. 12, Nov. 2011, pp. 8571-8584.

Matsumoto, Celso S. et al., Pattern Visual Evoked Potentials Elicited by Organic Electroluminescence Screen, BioMed Research International, Aug. 2014, pp. 1-6.

Potts et al., The Electrically Evoked Response of the Visual System (EER), Investigative Ophthalmology & Visual Science, vol. 7, No. 3, Jun. 1968, pp. 269-278.

Viswanathan, Suresh et al. The Uniform Field and Pattern ERG in Macaques With Experimental Glaucoma: Removal of Spiking Activity, Investigative Ophthalmology & Visual Science, vol. 41, No. 9, Aug. 2000, pp. 2797-2810.

* cited by examiner

| DTL thread Position | Relative Electrical Potential |
|---|---|
| A | 100% |
| B | 75% |
| C | 60% |
| D | 55% |
| E | 45% |
| F | 0-20% |

METHOD AND APPARATUS FOR PERFORMING ELECTRORETINOGRAPHY, INCLUDING ENHANCED ELECTRODE

REFERENCE TO PENDING PRIOR PATENT APPLICATION

This patent application claims benefit of prior U.S. Provisional Patent Application Ser. No. 63/157,272, filed Mar. 5, 2021 by Diagnosys LLC and Jeffrey D. Farmer et al. for ENHANCED DTL ELECTRODE.

The above-identified patent application is hereby incorporated herein by reference.

FIELD OF THE INVENTION

This invention relates to ophthalmic psychophysical diagnostic equipment in general, and more particularly to new and improved methods and electrodes for performing electroretinography.

BACKGROUND OF THE INVENTION

Ophthalmic electrophysiology diagnostic equipment, such as that manufactured and sold by Diagnosys LLC of Lowell, MA, is typically used to stimulate the eye of a test subject using flashes (or moving patterns) of light, and then to measure the resulting electrical response generated at the retina of the test subject (i.e., to obtain an electroretinogram, or "ERG"). Additionally, such ophthalmic equipment may be used to stimulate the eye of a test subject and, by using electrodes applied on or near the eye, obtain and measure the electrical response generated at the visual cortex (i.e., to obtain a visual evoked potential, or "VEP") using electrodes applied on (or near) the visual cortex. To that end, electrodes (sometimes referred to as "reference electrodes" and "ground electrodes") may be applied to other locations of the test subject's body in order to make electrical measurements that are important for performing the electroretinography test.

Ophthalmic electrophysiology is considered to be the only objective measure of visual function; all other ophthalmic diagnostics are either subjective measures of visual function, or a measure of anatomical structure.

There are a wide array of standard electroretinography (ERG) tests that may be performed on a test subject, including full-field ERG, pattern ERG, multi-focal ERG, focal ERG, etc. Similarly, for tests of visual evoked potential (VEP), available options include the pattern reversal VEP, pattern onset VEP and flash VEP.

With both ERG and VEP tests, the test is typically conducted by exposing one or both of the test subject's eyes to multiple flashes of light (or moving patterns of light), and recording a corresponding number of electrical response readings from the eye of the test subject. An average of the individual responses recorded is then typically calculated and reported as a single test result.

An exemplary system 5 for performing ERG on a test subject is shown in FIGS. 1 and 2.

System 5 generally comprises a stimulator 10 (e.g., a monitor (FIG. 1), a ganzfeld bowl stimulator (FIG. 2), flash paddle or other similar device that produces light), a plurality of electrodes 15 for recording electrical responses from the eye(s) of the test subject, an amplifier 20 for amplifying electrical signals obtained by plurality of electrodes 15, a controller 25 for receiving electrical signals from amplifier 20 and for controlling operation of stimulator 10, and a computer 30 running appropriate software for controlling controller 25.

Plurality of electrodes 15 generally comprises a ground electrode 35 for contacting the skin of the test subject at a location away from the eye(s) of the test subject (e.g., the temple), a right eye reference electrode 40 for contacting the skin of the test subject proximate to the right eye of the test subject, a right eye active electrode 45 for contacting the right eye of the test subject, a left eye reference electrode 50 for contacting the skin of the test subject proximate to the left eye of the test subject, and a left eye active electrode 55 for contacting the left eye of the test subject. In this manner, plurality of electrodes 15 may be used to record the electrical response of the test subjects' eye(s) upon stimulation of the eye(s) using stimulator 10 (and to link those electrical responses to the stimulation that is performed), resulting in an electroretinogram that can be assessed by a clinician (or researcher).

A system similar to system 5 is typically used for obtaining visual evoked potential (VEP) recordings, however, when system 5 is used to obtain VEP recordings, an active electrode (not shown) is typically disposed on the scalp of the test subject above the area of the test subject's brain associated with the visual cortex, and active electrodes 45, 55 on the eye(s) of the test subject may be omitted. It will also be appreciated that system 5 may be modified to provide various combinations of electrodes for both ERG and VEP recordings, which combinations will be apparent to one of ordinary skill in the art. See, for example, the international standards and publications found at www.iscev.org, a website published by the International Society for Clinical Electrophysiology of Vision (ISCEV).

When performing ERG or VEP tests, the human test subject being tested is typically awake (i.e., conscious) during the test. The test subject is instructed to remain still during the test, and is typically also instructed to look straight ahead at a fixation point (e.g., a fixation point displayed on stimulator 10). The purpose of an ERG or VEP test is to record the electrical response of the retina of the test subject's eye (ERG) and/or that of the visual pathway in a human brain ending at the visual cortex (VEP).

However, with even the most relaxed test subject, fixating as intently as possible and attempting not to move their body, artifacts arise during the test which are recorded by the plurality of electrodes 15 and/or amplifier 20 of system 5. As used herein, such "artifacts" are intended to refer to any electrical signals recorded by the plurality of electrodes 15 or amplifier 20 which do not originate in the retina or visual pathway from the eye to the brain's visual cortex.

Many artifacts are known and understood, described in the literature, and handled by existing ophthalmic electrophysiology systems. By way of example but not limitation, such artifacts may include electrical noise (i.e., electromagnetic interference) that comes from other machines in the area around the testing equipment (which artifacts typically oscillate at the frequency of the electrical main power supply used in the region of the world where the test equipment is situated, typically 50 or 60 hz cyclical noise). Given the reasonably consistent frequency of this artifact source, there are well known ways to reject and/or filter out the noise from other machines.

Another common artifact is generated by the test subject blinking during the performance of the test. A typical human will blink approximately one time every 10 seconds. During an ERG test, which can last between 1 to 5 minutes, the test subject may blink many times. The electrical signal generated by the test subject's blink (and measured by the plurality of electrodes 15 and/or amplifier 20) is generally quite substantial when compared to even the largest ERG or VEP electrical signal. A blink by the test subject results in an electrical artifact that is recorded by the electrode by either moving the electrode, or by recording the muscular electrical signals associated with the blink, or both. The recorded amplitude coming from a blink is usually 1 millivolt or larger. ERG and VEP signal amplitudes are typically in the range of 1 to 200 microvolts (μV), and usually no larger than 500 μV. A common way of rejecting signals that result from the test subject's blinks is to manually (or automatically) reject recorded sweeps with amplitudes larger than +/−1 millivolt, or similar levels depending on the specifics of the test.

Given that many biological electrical artifacts emanate from the area around the eye of a test subject due to eye movements, pupillary movements, muscle contractions and the relatively close proximity of the ERG electrodes to those sources of artifacts, the ERG can be significantly affected by even small muscle artifacts.

The ERG has historically been used primarily to measure the function of photoreceptor, bipolar, amacrine and retinal ganglion cells in the retina of the eye. In normal (and most diseased) test subjects, electrical signals (i.e., responses) occur within 50 milliseconds (ms), or less, after the optical flash or pattern rotation stimulus of the ERG test has been presented to the eye(s) of the test subject. Most muscle responses that generate electrical artifacts due to the optical stimulus itself will typically occur at 100 ms (or later), after the optical flash or pattern rotation stimulus has been presented to the eye(s) of the test subject. The fastest muscle responses recorded in a human test subject occurred at approximately 55 ms after the optical flash or pattern rotation stimulus had been presented to the eye(s) of the test subject, but the muscle response can also happen randomly at any point during the recording.

Typically these artifacts come from very slight eye movements and/or eye twitches that can occur randomly or in-phase with the optical stimuli (i.e., they are caused by, and at a relatively constant time after, the optical stimuli). The artifacts overlap in time and frequency with the ERG retinal response. This is a significant confounding factor in correctly measuring the ERG retinal response of a test subject.

More particularly, the plurality of electrodes 15 (e.g., the aforementioned electrodes 35, 40 45, 50) and amplifier 20 of system 5 are typically configured to record all electrical signals that are detected by the electrodes during a test, at all electrical resonant frequencies. Generally, some filtering of frequencies that are not of interest is done during signal recording or in post-analysis of the resulting electroretinogram (e.g., via computer 30). Typically, and according to the international ISCEV standard, the ERG and VEP recordings are performed with a bandpass filter set at as wide as 0.3 to 300 hz (i.e., to remove data with frequencies that occur below 0.3 hz or above 300 hz), and as narrow as 1 to 100 hz (i.e., to remove data with frequencies that occur below 1 hz or above 100 hz), which filter acts to automatically filter out signals that are likely to be artifacts. For example, the ISCEV international standard specifies the following bandpass filter for the standard ERG: "The system should record frequencies that include at least the range from 0.3 to 300 Hz". And the ISCEV international standard specifies the following bandpass filter for the standard VEP: "The recording frequency band of bandpass amplifiers should include the range from 1 to 100 Hz". Finally, the ISCEV international standard specifies the following bandpass filter for the standard PhNR (i.e., functional test of ganglion cells): "The low-frequency filter should be 0.3 Hz or lower; the high-frequency filter, a minimum of 300 Hz".

The typical response frequencies of the test subject's retina to an optical stimulus flash, and the typical response frequencies that tend to occur from muscle artifacts recorded by the ERG electrodes, can overlap in their frequency ranges. Most of the electrical energy recorded from the retina has a frequency in the range of 1 to 100 hz, with the majority of that energy falling in the range of 10 to 60 hz. Most of the electrical energy recorded from the eye muscle artifacts, such as eye twitches and slight eye movements, has a frequency in the range of 1 to 20 hz, with the majority of that energy in the range of 1 to 10 hz.

Eye muscle artifacts create electrical signals that can look very similar to retinal signals, or at a minimum will detract highly from the ability to observe the retinal signal. Artifact signals can overlap in time and frequency space, and are therefore a significant confounding factor to conducting an accurate ERG measurement of retinal function of a test subject.

In some cases, clinicians recognize the presence of eye muscle artifacts in a test and discard the test altogether, resulting in wasted time by the test subject, technician, and clinician, with no valid test being recorded. In other cases, the clinician does not recognize the presence of artifacts in a test, resulting in a strong possibility of an incorrect interpretation and, in the worst case, an incorrect diagnosis of disease or health. Except for very highly trained test subjects, these types of muscle artifacts are unavoidable during the test, even when the subject tries their very best to avoid generating them.

Thus, there exists a need for a new and improved ERG active electrode that helps to minimize the recording of signals from artifacts.

A common active electrode currently used for ERG tests is the DTL (or DTL Plus) electrode invented by William W. Dawson, Gary L. Trick and Carl A. Litzkow, after whom the electrode is named through its acronym "DTL", which electrode is the subject of U.S. Pat. No. 4,417,581. Exemplary DTL electrodes 60 are shown in FIGS. 3 and 4 of the present application. Both of the DTL electrodes shown in FIGS. 3 and 4 comprise thin (typically 8-50 micron in diameter) conductive threads 65 fixed between two sticky pads 70, 75.

Typically, conductive threads 65 of a DTL electrode comprise one or more conductive threads 65 (i.e., 1 thread or up to 7 conductive threads, or more). Conductive threads 65 may be formed as nylon threads coated with a very thin layer of (conductive) medical grade silver, but other thread and conductive layer materials may be used if desired. Using a plurality of conductive threads 65 (i.e., more than one conductive thread) improves strength integrity; if one conductive thread breaks, the remaining conductive threads are still able to carry the electrical signal.

Sticky pads 70, 75 typically comprise a foam upper layer 80 and a foam lower layer 85, with each of the two layers of foam 80, 85 being about 1-2 mm thick. Conductive thread(s) 65 are typically fixed (e.g., with adhesive) between foam upper layer 80 and foam lower layer 85. An electrical cable and connector 90 (FIG. 3), or an electrical connector pin 95 (FIG. 4), is also fixed (e.g., with an adhesive) between upper layer 80 and lower layer 85 of sticky pads 70, 75, and is in physical and electrical contact with the conductive thread(s) 65 (e.g., at a location between foam upper layer 80 and foam lower layer 85 of sticky pads 70, 75). Sticky pads 70, 75 comprise an appropriate adhesive that is safe for contact with human skin on their bottom side (i.e., on the surface of foam lower layer 85 that contacts the skin of the patient/test subject), whereby to permit sticky pads 70, 75 to be attached to the skin in the area of the eye (and to be removed after the test is complete).

FIG. 5 shows an exemplary placement of a DTL electrode 60 relative to a human eye. Sticky pads 70, 75 are affixed to the face of the test subject on either side of the eye such that conductive thread 65 is in contact with the eye at a location just below the cornea, near the conjunctiva, resting near the top edge of the lower eye lid. Note that conductive thread 65 of DTL electrode 60 of FIG. 5 is indicated with a bold, black graphical line to help show where the thin thread is located. Conductive thread 65 of DTL electrode 60 is configured to be in electrical contact with the eye of the test subject through its contact with either natural tear film and/or artificial tears dropped onto the eye before performing the ERG test.

To date, DTL electrodes have only been used in a monopolar format. That is, in all ERG recordings, an electrical voltage potential is measured (e.g., using DTL electrode 60) after optically stimulating the retina and, in every case, the value recorded by the ERG system is the difference in electrical potential measured between two electrodes (i.e., an active electrode and a reference electrode). In the case of a monopolar DTL electrode 60, the DTL electrode serves as one electrode (i.e., the active electrode) and a second, separate electrode is placed on the skin and serves as the reference electrode (see, for example, FIGS. 1 and 2, which show reference electrodes 40, 50 placed on the skin of the test subject in the region of the test subject's eye). Electrical voltage potentials reported on the ERG system are the difference in potential measured by the active electrode and the reference electrode after retinal stimulation. Typical locations for the reference electrode are on the skin near the temporal canthus of the eye of the test subject, on the temple of the test subject, on the forehead or ear lobe of the test subject, etc.

Electrodes used to record the ERG active signal need to balance electrode performance with patient safety and comfort. Both performance and comfort need to be optimized in order to obtain reliable and repeatable results.

More particularly, electrodes which are to be used to record the active ERG signal must be placed as close to the stimulated source of interest (e.g., the retina) as possible. Unfortunately, although a DTL electrode having a conductive thread disposed on the apex of the cornea yields the largest active signal, such placement is also the least comfortable for the test subject. Thus, the challenge is to balance signal strength with test subject comfort.

Different electrode designs have been created that fall into three general categories (identified by where the electrode is placed): (i) contact lens electrodes, (ii) conjunctival electrodes, and (iii) skin electrodes.

A comparison of relative electrode signal strengths among the three general types of electrodes reveals that if the contact lens records an amplitude of 100 percent, the conjunctival electrode recording of the same ERG would be approximately 80 percent, while the skin electrode recording would be roughly somewhere between 25-35 percent. It is worth noting that although signal strength may be affected by the type of electrode used, signal timing and waveform are largely unaffected.

In conjunction with signal strength, the signal-to-noise ratio is also a significant factor to be considered when seeking quality ERG results. Noise may be introduced into the signal by inherent electrode properties that influence connection quality (i.e., impedance). By way of example, contact lens and conjunctival electrodes are placed directly on the surface of a moist eye that is inherently conductive. By contrast, skin electrodes accrue greater background noise since the electrical signal must travel through skin before reaching the electrode.

Contact lens electrodes generally record the largest ERG amplitudes because the active electrode is in constant contact with the cornea, encircling the apex of the eye. However, since contact lens electrodes hold the eye open to prevent blinking, many test subjects may find them uncomfortable or intimidating. Topical anesthesia is always used, and younger test subjects are generally sedated.

While contact lens electrodes can be used for several hours at a time, a session of 30 minutes or less is what is generally practical for most test subjects (Heckenlively, 2006). Prolonged recordings utilizing contact lens electrodes tend to increase the risk of corneal abrasions, conjunctival abrasions, and irritation from the lens moving against the cornea. Notably, the contact lens electrode adds a layer of material atop the cornea, which alters a patient's refraction. Therefore, contact lens electrodes are not suitable for use for pattern ERG (PERG) tests.

The most common contact lens electrodes in use today are Hansen Ophthalmic's Burian Allen electrode and Fabrinal's Jet electrode.

The Burian Allen electrode is provided as a reusable contact lens electrode manufactured by Hansen Ophthalmic Development Laboratory of Bellingham, WA The Burian Allen contact lens electrodes are available in eight different sizes ranging from adult to premature infant. Additionally, there are two types of Burian Allen electrode: unipolar and bipolar. A bipolar Burian Allen electrode includes both active and reference electrodes in a single contact lens electrode, while a unipolar lens contains only the active electrode.

The Jet electrode is considered a single-use contact lens electrode, and contains only an active electrode. It is smaller and slightly more comfortable for the test subject to wear than the Burian Allen contact lens electrode, but the Jet electrode is less secure on the eye and can be more easily blinked out by the test subject.

Conjunctival electrodes are placed on the eye of the test subject, however, instead of covering the cornea, conjunctival electrodes are configured to lay mostly in the conjunctiva. Researchers developed conjunctival electrodes in order to create a more patient-friendly alternative to the contact lens-style electrodes. Many clinicians consider conjunctival electrodes to be the best at optimizing both performance and comfort. Topical anesthesia is typically not required for use of a conjunctival electrode, but may be necessary depending on the patient. Conjunctival electrodes can be worn comfortably for longer periods of time than contact lens electrodes because their small size allows patients to blink freely.

In addition, conjunctival electrodes do not alter the patient's refraction, making them ideal for performing tests such as a pattern ERG (PERG) test. Consistent placement of conjunctival electrodes is important in order to obtain reliable and repeatable test results.

Currently, the most popular conjunctival electrodes are the DTL Plus electrode, the gold foil electrode (invented by Carter & Hogg of the UK), and the H-K Loop electrode (invented by Hawlina and Konec of Slovenia). All three of these electrodes (i.e., the DTL Plus electrode, the gold foil electrode and the H-K Loop electrode) are monopolar electrodes.

The single-use DTL Plus electrode utilizes two small adhesive pads to secure the DTL Plus electrode to the test subject, with one pad disposed at the nasal area, and the other pad disposed at the temporal canthi. The conductive thread (i.e., a single conductive thread or a plurality of conductive threads) of the DTL Plus electrode drapes across the sclera, usually along the lower lid. This position is known as the lower lid position (LLP). The DTL Plus electrode can also be placed such that the conductive thread of the electrode is disposed lower into the fornix, which is known as the fornix position (FP). A recent study compared the two electrode placements, and found that the LLP records higher amplitudes while the FP is more comfortable (Brouwer, 2020). What is most important is to choose one of the positions, and ensure that the electrode remains in that position throughout the recording (i.e., throughout the ERG test). DTL Plus electrodes excel in the area of test subject/patient comfort, reduced noise and artifact, optical quality, and low electrode impedance. DTL Plus electrodes also eliminate the risk of corneal abrasions and conjunctival infections. It has been found that the vast majority of test subjects prefer DTL Plus electrodes to any other type of electrode for comfort.

The gold foil electrode is a reusable electrode made of flexible mylar-gold that is "hooked", or shaped around and placed under, the lower eyelid of the test subject. A gold foil electrode may come into contact with the corneal-scleral junction on the midline. Although reusable, sterilizing gold foil electrodes can be challenging, and there is disagreement among researchers about whether electrodes reused more than three times produce decreased amplitudes.

The reusable H-K Loop electrode consists of a thin, molded looped wire that fits into the lower conjunctival sac. Electrical contact is made with the scleral conjunctiva through an exposed portion of an otherwise insulated wire. Due to its shape, the loop of an H-K Loop electrode does not come into contact with the corneal surface.

Skin electrodes used as the active ERG electrode are placed on the skin of the test subject directly beneath the eye. ERG amplitudes measured by skin electrodes are significantly less than both contact lens electrodes and conjunctival electrodes. ERGs recorded using a skin electrode are small and quite variable in amplitude because the eye-to-skin current pathway contains high and varying resistances. (Arden, 1979). The impedance when using skin electrodes is naturally quite high. To lower the impedance, the skin beneath the electrode must be carefully scrubbed to remove all oils and dead skin cells. Larger skin electrodes require larger areas of skin to be prepped; this preparation must be done well or noise may conceal the ERG signal.

In summary, there are a variety of reusable and single use skin electrodes commercially available that can be used as the ERG active electrode. Furthermore, there are skin electrodes that are bipolar, incorporating both the active and reference electrodes, and in some cases also the ground electrode.

An important aspect to measuring ERG voltage potentials of the retina is the fact that voltage potentials differ depending on where the measurement is taken. In the case of an ERG test, the retina is stimulated with an optical source, and the retina generates an electrical current. This electrical current flows in all directions, emanating from the retina. Importantly, for ERG recordings, electrical current flows from the retina forward through the eye, and tends to create the largest voltage potential at the surface of the eye within the pupil. The voltage potential drops off to lower values away from the pupil, reaching its lowest values near the fornix of the eye (in terms of practical locations where an electrode can measure an ERG potential on the eye). ERG voltage potentials can be measured on the inside of the eyelid and on the skin near the eye, but at progressively lower levels further way from the center of the eye and also progressively lower levels as the current needs to travel further through the skin away from the eye. FIG. 6 shows a schematic of the human eye and eyelids, along with typical locations used with DTL conductive thread electrodes, together with a table of approximate relative electrical potentials typically measured at five (labeled A-F) positions on and near the eye, scaled from 100% at the largest potential on the surface of the eye in the center of the pupil.

As discussed above, compared to all other types of ERG electrodes, the DTL electrode excels in the area of patient comfort, reduced noise and artifacts, optical quality, and low electrode impedance. The DTL electrode also eliminates the risk of corneal abrasions and conjunctival infections.

However, one significant limitation of DTL electrodes is that DTL electrodes are currently only available as monopolar active electrodes, with no option for combined active-plus-reference bipolar electrodes (with or without also incorporating a ground electrode). Another limitation of current DTL electrodes is that the active measurement surface (i.e., the conductive silver coated thread(s) of the DTL electrode) spans a large range across the eye, thereby causing the measured signal to come from a large, averaged surface area, across the entire eye. A further limitation of DTL electrodes has been the lack of different options for the shape of the pads which hold the conductive thread of the DTL electrode in place, thereby limiting options for accurate placement of the thread on the eye.

Thus, there is a need for a new and improved DTL-style electrode comprising (i) a bipolar electrode, (ii) a conductive thread configured to measure the electrical response of only a select portion of the region of the eye contacted by the conductive thread, and/or (iii) sticky pads for mounting the novel electrode in place which permit a wider range of options for accurate placement of the electrode relative to the test subject's eye.

SUMMARY OF THE INVENTION

The present invention comprises the provision and use of a new and improved DTL-style electrode comprising (i) a bipolar electrode, (ii) a conductive thread configured to measure the electrical response of only a select portion of the region of the eye contacted by the conductive thread, and/or (iii) sticky pads for mounting the novel electrode in place which permit a wider range of options for accurate placement of the electrode relative to the test subject's eye.

In one preferred form of the invention, there is provided apparatus for use in performing electroretinography on a test subject, the apparatus comprising:

at least one electrically conductive thread, the at least one electrically conductive thread comprising a first end and a second end, wherein the first end of the at least one electrically conductive thread is configured to mount to skin on one side of an eye of the test subject and the second end is configured to mount to skin on the opposite side of the eye of the test subject, such that the at least one electrically conductive thread is in contact with a surface film of an eye; and an electrically non-conductive coating applied to at least one region of the at least one electrically conductive thread, whereby to electrically isolate the at least one region of the at least one electrically conductive thread from the eye.

In another preferred form of the invention, there is provided a method for performing electroretinography on a test patient, the method comprising:

providing apparatus comprising:

least one electrically conductive thread, the at least one electrically conductive thread comprising a first end and a second end, wherein the first end of the at least one electrically conductive thread is configured to mount to skin on one side of an eye of the test subject and the second end is configured to mount to skin on the opposite side of the eye of the test subject, such that the at least one electrically conductive thread is in contact with a surface film of an eye; and an electrically non-conductive coating applied to at least one region of the at least one electrically conductive thread, whereby to electrically isolate the at least one region of the at least one electrically conductive thread from the eye;

mounting the first end of the at least one electrically conductive thread to the skin on one side of an eye of the test subject, and mounting the second end of the at least one electrically conductive thread to the skin on the opposite side of the eye of the test subject, such that the at least one electrically conductive thread is electrically isolated from the skin, and such that at least one region of the electrically conductive thread is in electrical contact with the eye of the test subject.

In another preferred form of the invention, there is provided apparatus for use in performing electroretinography on a test subject, the apparatus comprising:

at least one electrically conductive thread, the at least one electrically conductive thread comprising a first end and a second end, wherein the first end of the at least one electrically conductive thread is configured to mount to a first sticky pad and the second end of the at least one electrically conductive thread is configured to mount to a second sticky pad, wherein the first sticky pad is configured to mount to skin on one side of an eye of the test subject, and the second sticky pad is configured to mount to skin on the opposite side of the eye of the test subject;

wherein the second sticky pad comprises a top surface and a bottom surface, and further wherein the second sticky pad comprises a conductive element mounted to the bottom surface, whereby to make electrical contact with the skin when the second sticky pad is mounted to the skin.

In another preferred form of the invention, there is provided a method for use in performing electroretinography on a test subject, the method comprising:

providing apparatus comprising:

at least one electrically conductive thread, the at least one electrically conductive thread comprising a first end and a second end, wherein the first end of the at least one electrically conductive thread is configured to mount to a first sticky pad and the second end of the at least one electrically conductive thread is configured to mount to a second sticky pad;

wherein the second sticky pad comprises a top surface and a bottom surface, and further wherein the second sticky pad comprises a conductive element mounted to the bottom surface, whereby to make electrical contact with the skin when the second sticky pad is mounted to the skin;

mounting the first sticky pad to the skin of a test subject on one side of an eye of the test subject, and mounting the second sticky pad to the skin of the test subject on the opposite side of the eye of the test subject, such that the at least one electrically conductive thread is in electrical contact with the eye of the eye of the test subject;

wherein the at least one electrically conductive thread is configured to serve as the active electrode for performing electroretinography; and wherein the conductive element is configured to serve as the reference electrode for performing electroretinography.

In another preferred form of the invention, there is provided apparatus for use in performing electroretinography on a test subject, the apparatus comprising:

a sticky pad comprising a top surface and a bottom surface;

wherein the bottom surface of the sticky pad comprises an adhesive for mounting the sticky pad to skin of the test subject;

wherein the sticky pad is defined by a plane having a non-circular perimeter;

wherein the non-circular perimeter comprises a wide portion and a narrow portion, wherein the wide portion is configured to be positioned adjacent to the temple of the test subject, and the narrow portion is configured to guide a conductive thread mounted to the sticky pad toward the eye of the test subject.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
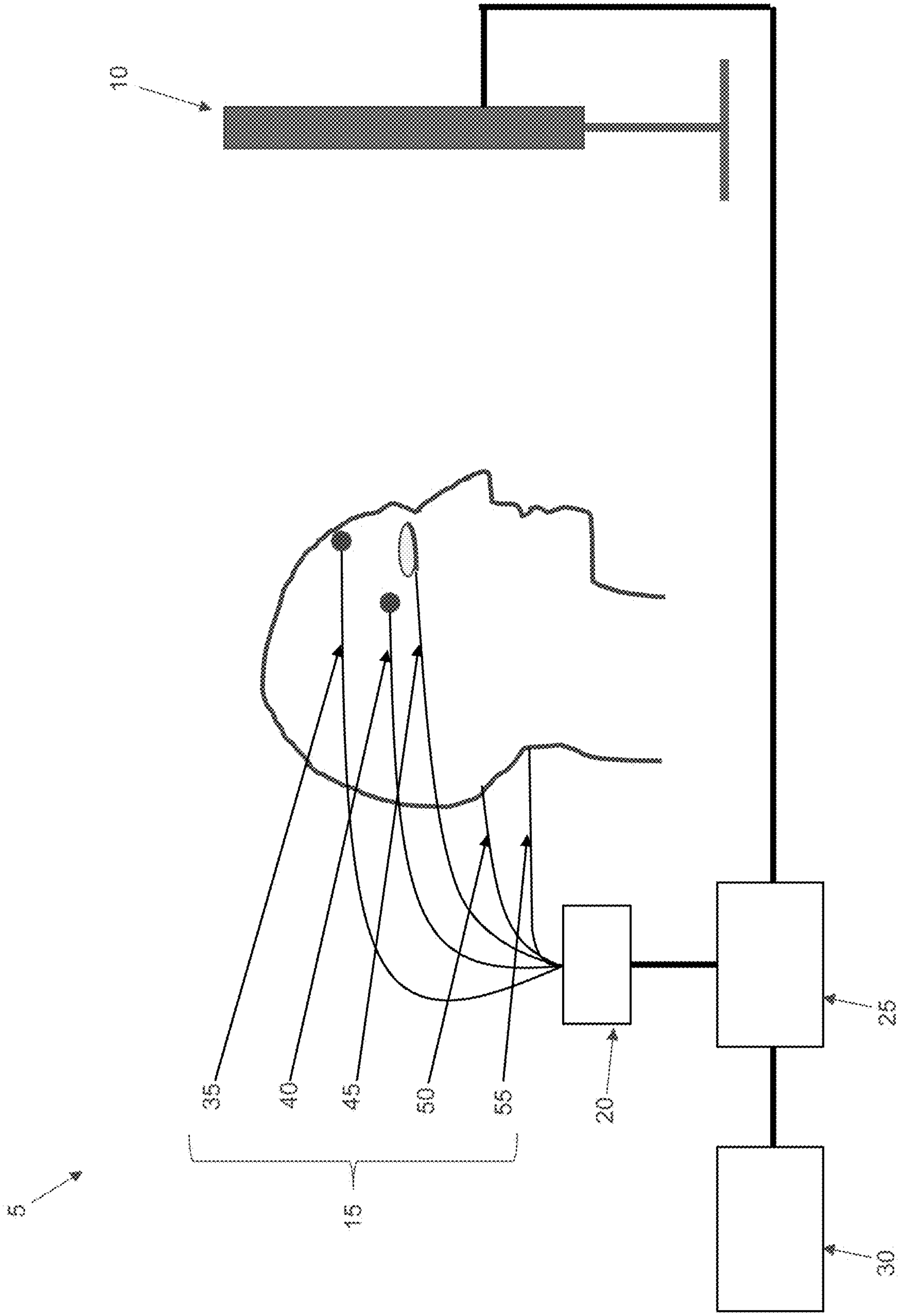
FIGS. 1 and 2 are schematic views showing an exemplary system for performing an ERG test on a test subject.
Figure 2:
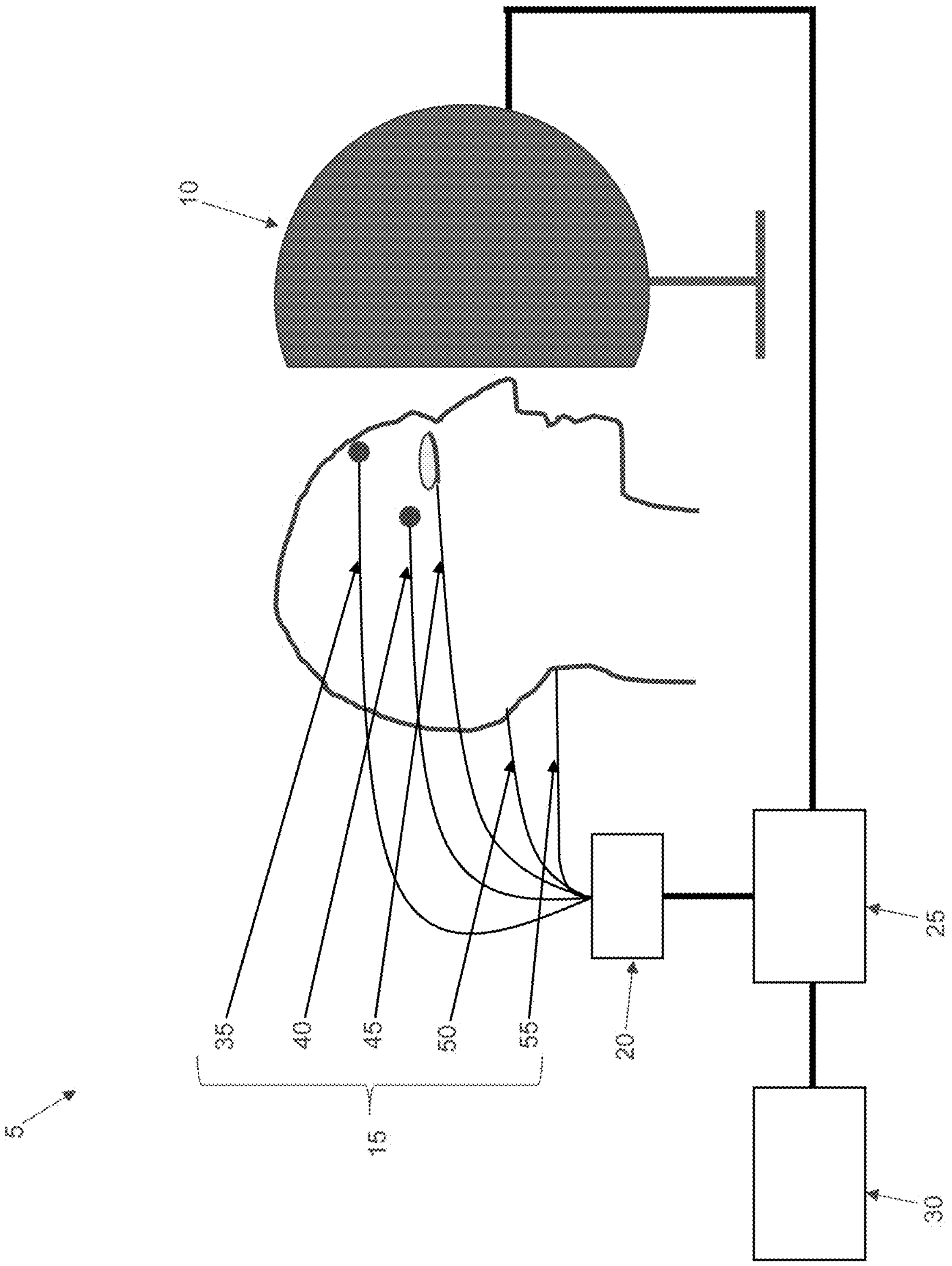
Figure 3:
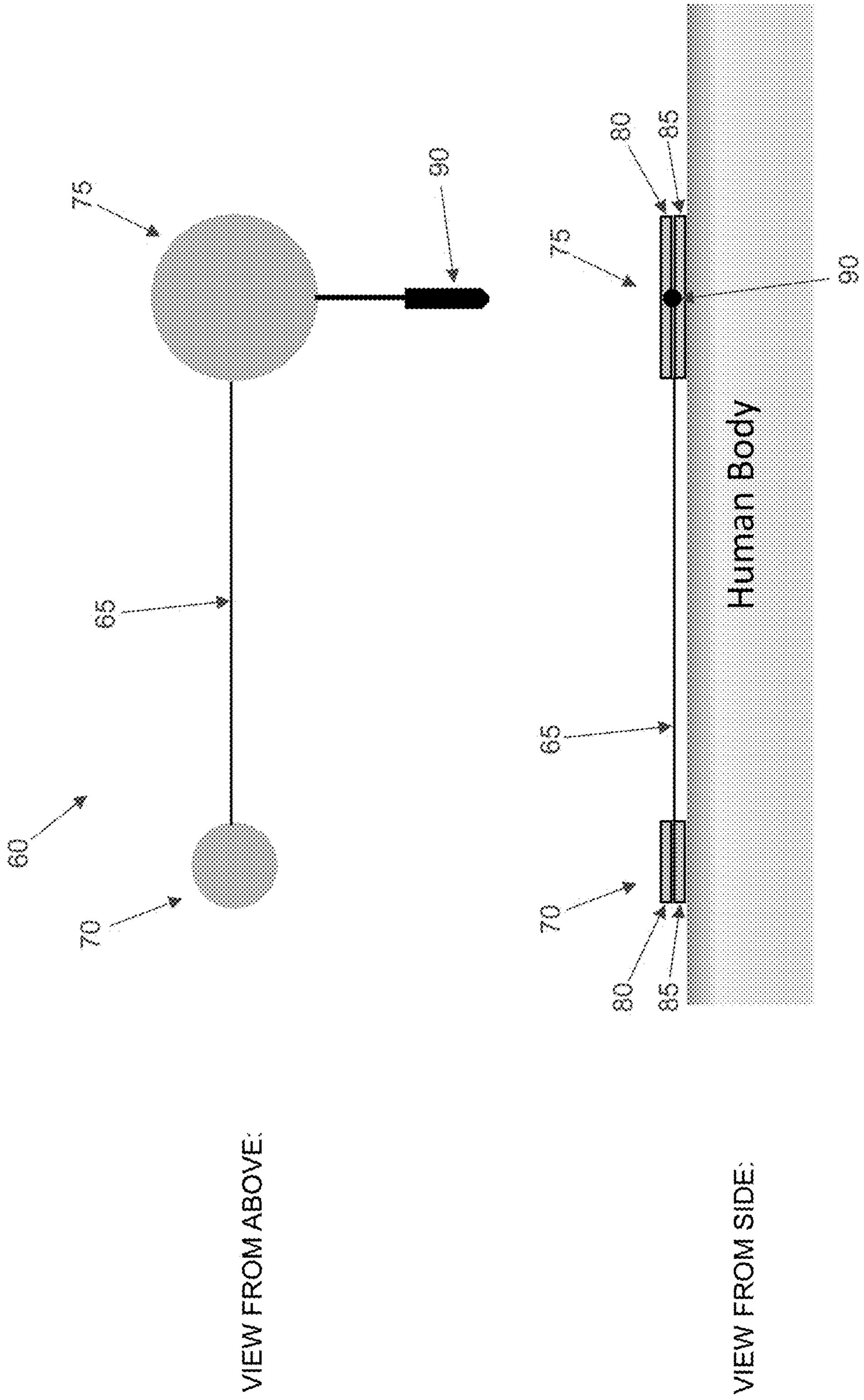
FIGS. 3 and 4 are schematic views of prior art DTL electrodes.
Figure 4:
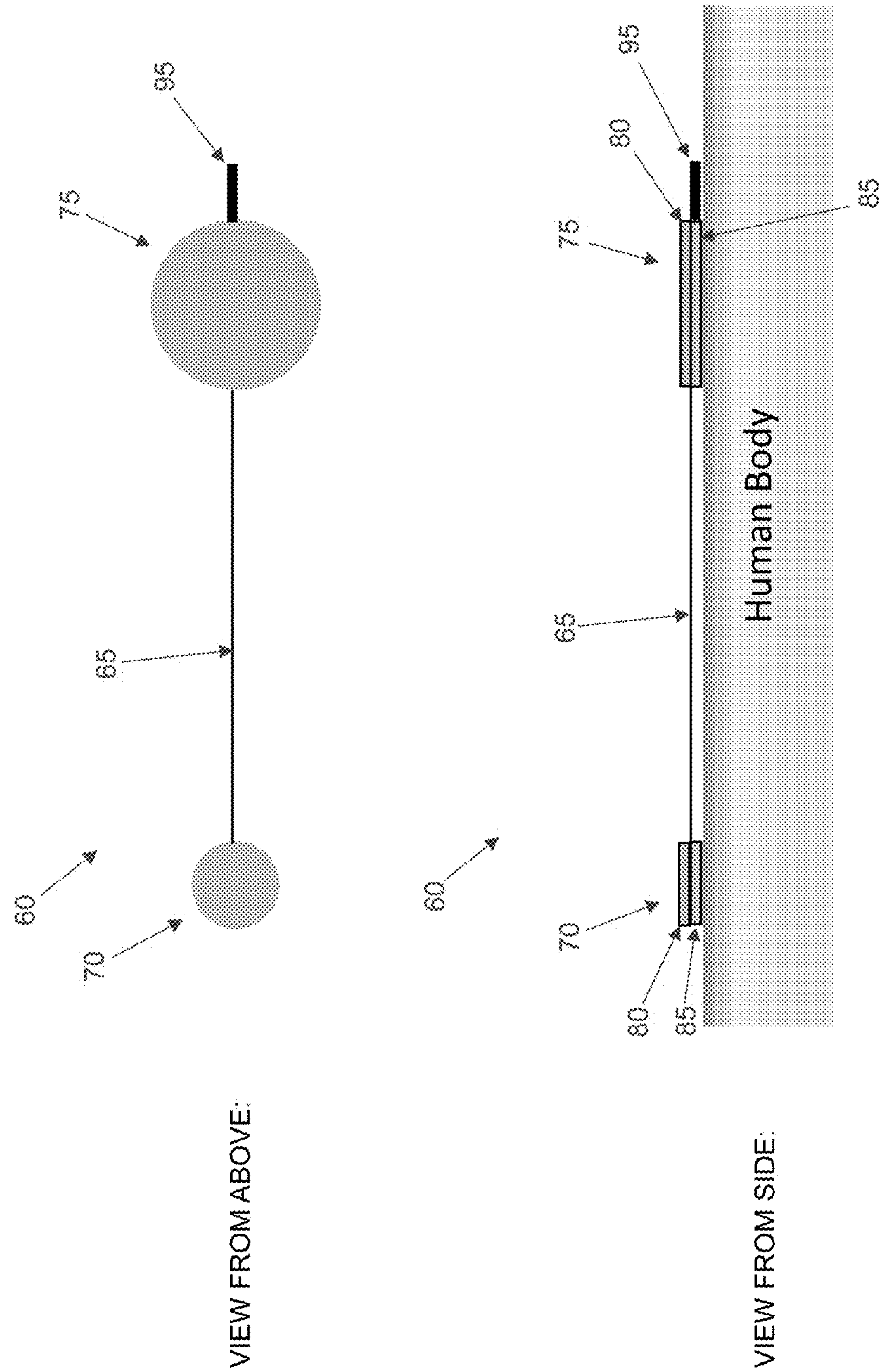

The present invention comprises the provision and use of a new and improved DTL-style electrode comprising (i) a bipolar electrode, (ii) a conductive thread configured to measure the electrical response of only a select portion of the region of the eye contacted by the conductive thread, and/or (iii) sticky pads for mounting the novel electrode in place which permit a wider range of options for accurate placement of the electrode relative to the test subject's eye.

More particularly, the present invention can be characterized by reference to three novel aspects that can be used independently of one another, or in combination with one another, in order to improve the performance, inter-session repeatability, and cost effectiveness of performing ERG tests when compared against use of a traditional DTL electrode.

To summarize, the first novel aspect of the present invention comprises the provision and use of an electrode comprising a thin coating of non-conductive material that is applied to the outer surface of a portion of the length of the conductive thread of the electrode. The second novel aspect of the present invention comprises the provision and use of a novel electrode that incorporates a reference electrode into the electrode, thereby creating a bipolar electrode. The third novel aspect of the present invention comprises the provision and use of sticky pads having new shapes and/or materials that are a part of, or next to, the sticky pads so as to permit a wider range of mounting options.

The novel electrode of the present invention may hereinafter be referred to as a "DTL electrode" or "DTL-style electrode", inasmuch as electrodes which mount to the eye in the manner of such prior art electrodes are commonly referred to as "DTL electrodes" by those of skill in the art. However, the novel electrode of the present invention is not a prior art DTL electrode, but merely mounts to the eye in a similar manner as existing DTL electrodes.

First Novel Aspect of the Invention: Non-Conductive Coating on Electrode Thread Looking now at FIGS. 7 and 8, there is shown a novel DTL-style electrode 100 formed in accordance with the present invention. Novel electrode 100 generally comprises a conductive thread 105, a first sticky pad 110 for mounting electrode 100 to the skin on one side of the eye of a test subject, and a second sticky pad 115 for mounting electrode 100 to the skin on the opposite side of the eye of the test subject. Conductive thread 105 may comprise a single conductive thread or, if desired, conductive thread 105 may comprise a bundle of conductive threads. A thin non-conductive coating 120 is applied to a portion of the outer surface of the conductive thread 105, whereby to electrically insulate that portion of the conductive thread from the anatomy, as will hereinafter be discussed in further detail. An electrical cable and connector 123 (FIG. 7), or an electrical connector pin 124 (FIG. 8) extends from second sticky pad 115 and is in electrical connection with conductive thread 105, whereby to permit electrode 100 to be connected to an amplifier and/or controller and/or computer in a manner that will be apparent to those of skill in the art in view of the present disclosure.

In one preferred form of the invention, non-conductive coating 120 is applied to conductive thread 105 at regions extending from the first and second sticky pads 110, 115 to a point near the center of the conductive thread, leaving an uncoated region 135 of conductive thread 105 uncoated where it will contact the cornea or the conjunctiva of the test subject, as will hereinafter be discussed. The use of non-conductive coating 120 on conductive thread 105 adjacent to sticky pads 110, 115 is primarily to improve the repeatability of placing the conductive (i.e., uncoated portion) of conductive thread 105 in the same position on the eye of the test subject each time electrode 100 is mounted to the test subject (i.e., to improve intersession repeatability) and also to isolate conductive thread 105 from electrical contact with the subject's skin and eye in locations that are not of primary interest in the ERG electrical potential measurement.

Conductive thread 105 of the novel electrode of the present invention may be provided in various forms. In one form of the present invention, non-conductive coating 120 comprises a material that can be thinly applied (e.g., a material that can be applied such that the resulting non-conductive coating 120 is only 1 to a few microns thick or thicker) to conductive thread 105 along a pre-defined length (i.e., in pre-defined regions) of the conductive thread.

If desired, electrode 100 may comprise two (or more) conductive threads 105, with each conductive thread 105 comprising one or more regions coated in non-conductive coating 120. By way of example but not limitation, in the case of a multi-thread electrode 100 (i.e., an electrode 100 comprising a plurality of conductive threads 105), non-conductive coating 120 may be applied to each conductive thread 105 individually, or non-conductive coating 120 may be applied to the entire bundle of conductive threads 105 at the same time.

Figure 7:
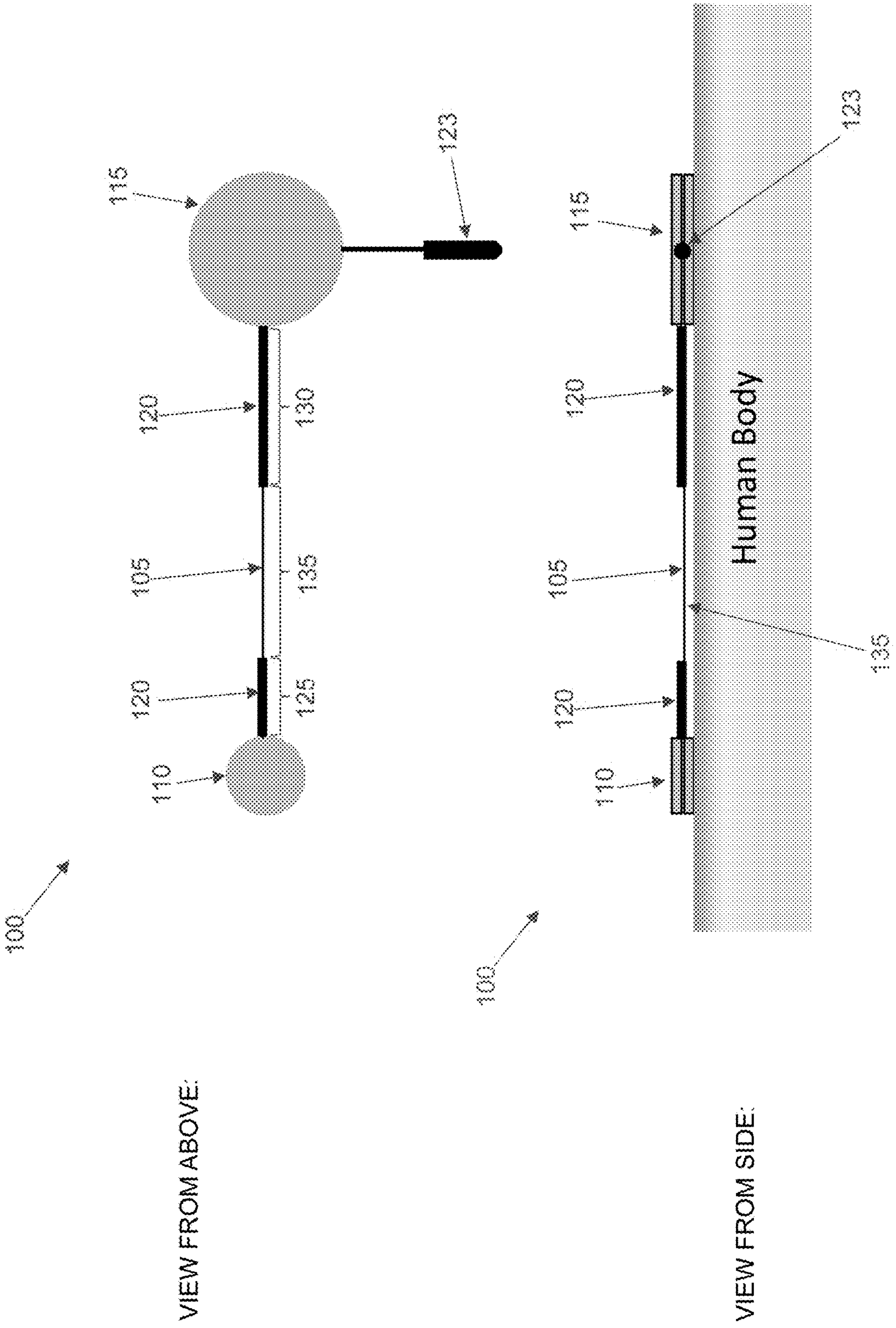
FIGS. 7 and 8 are schematic views showing a novel DTL-style electrode formed in accordance with the present invention.
Figure 8:
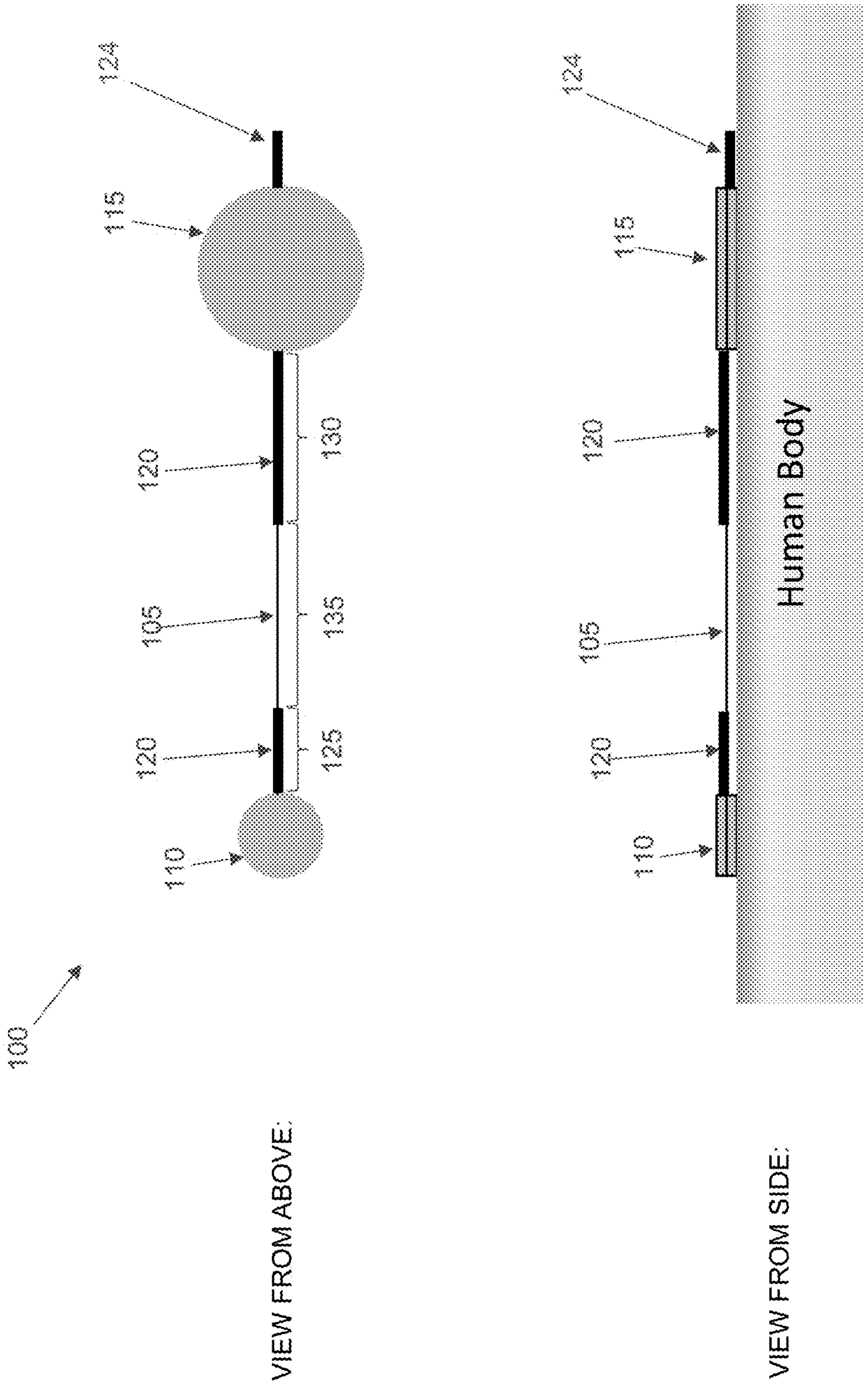
Figure 9:
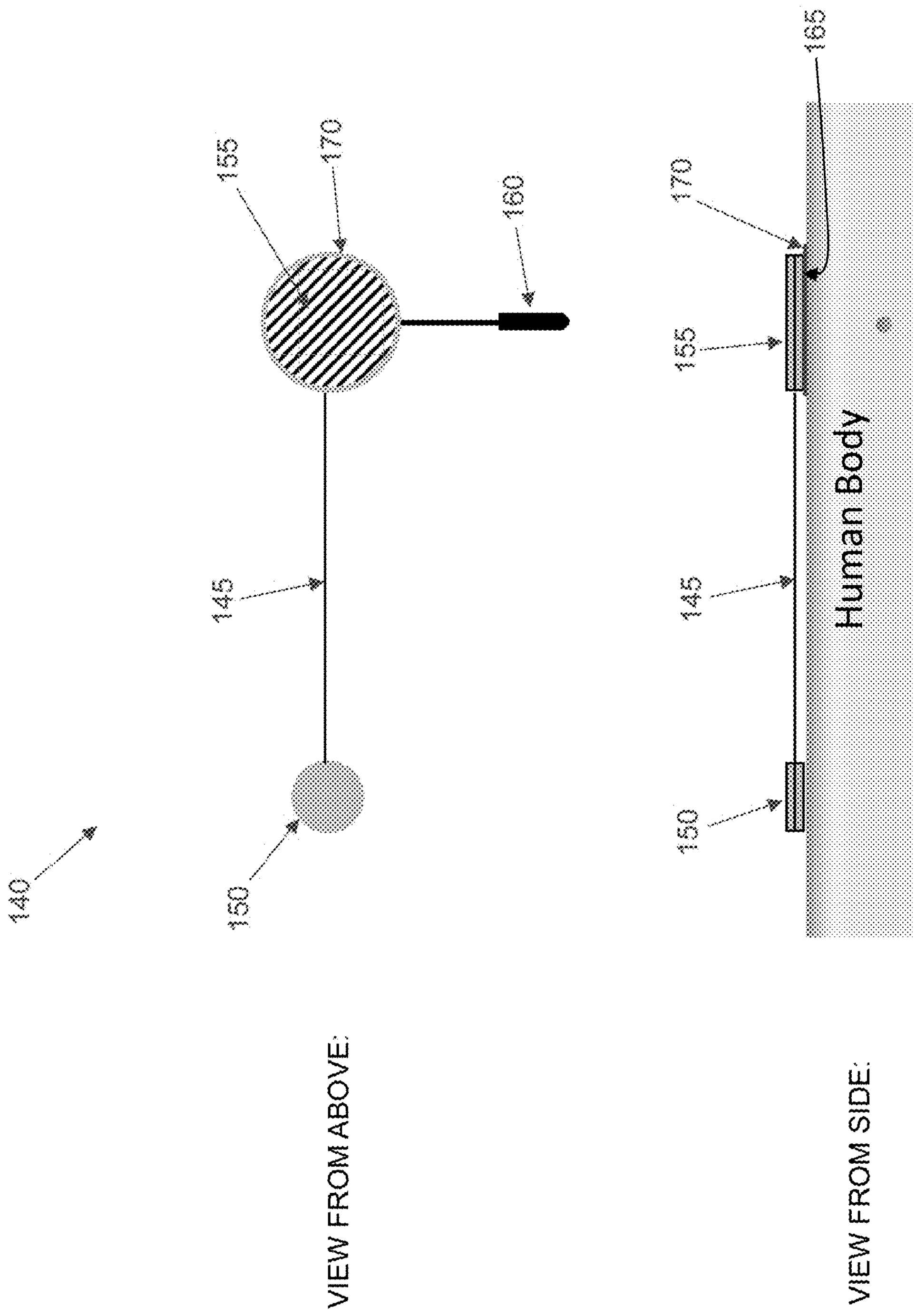
FIGS. 9, 9A, 10 and 10A are schematic views showing a novel bipolar electrode formed in accordance with the present invention.
Figure 9A:
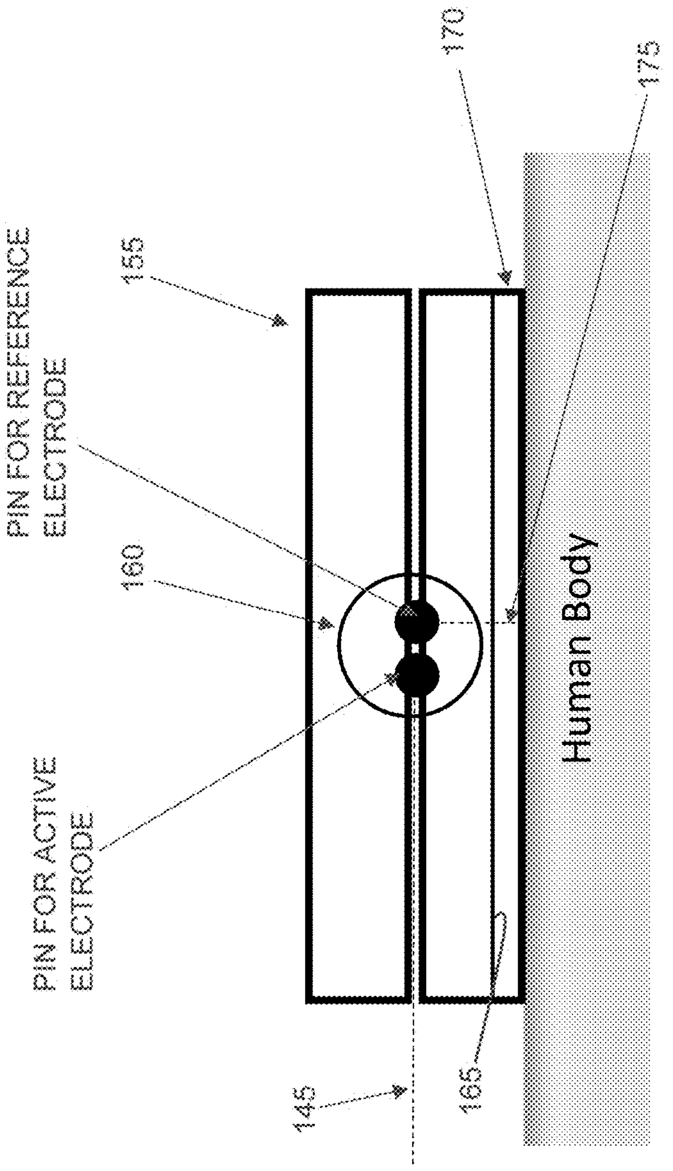
Figure 10:
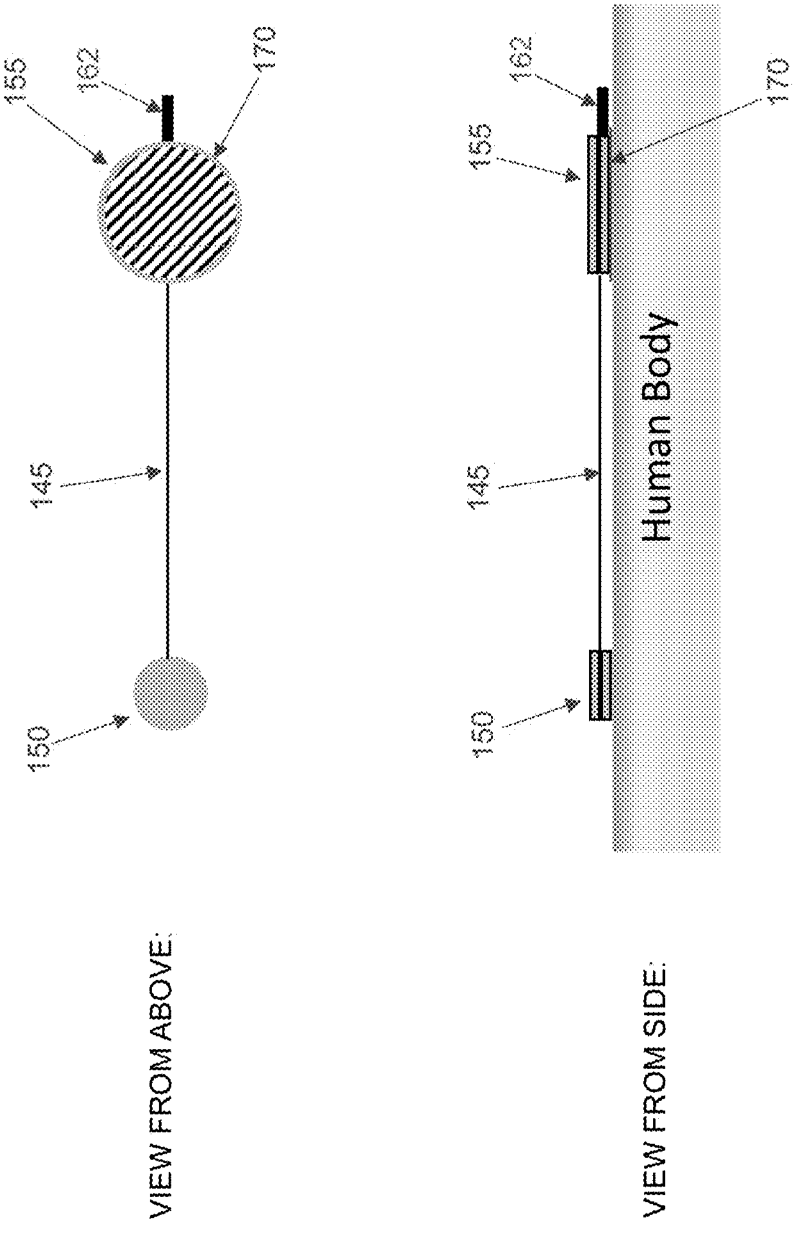
Figure 10A:
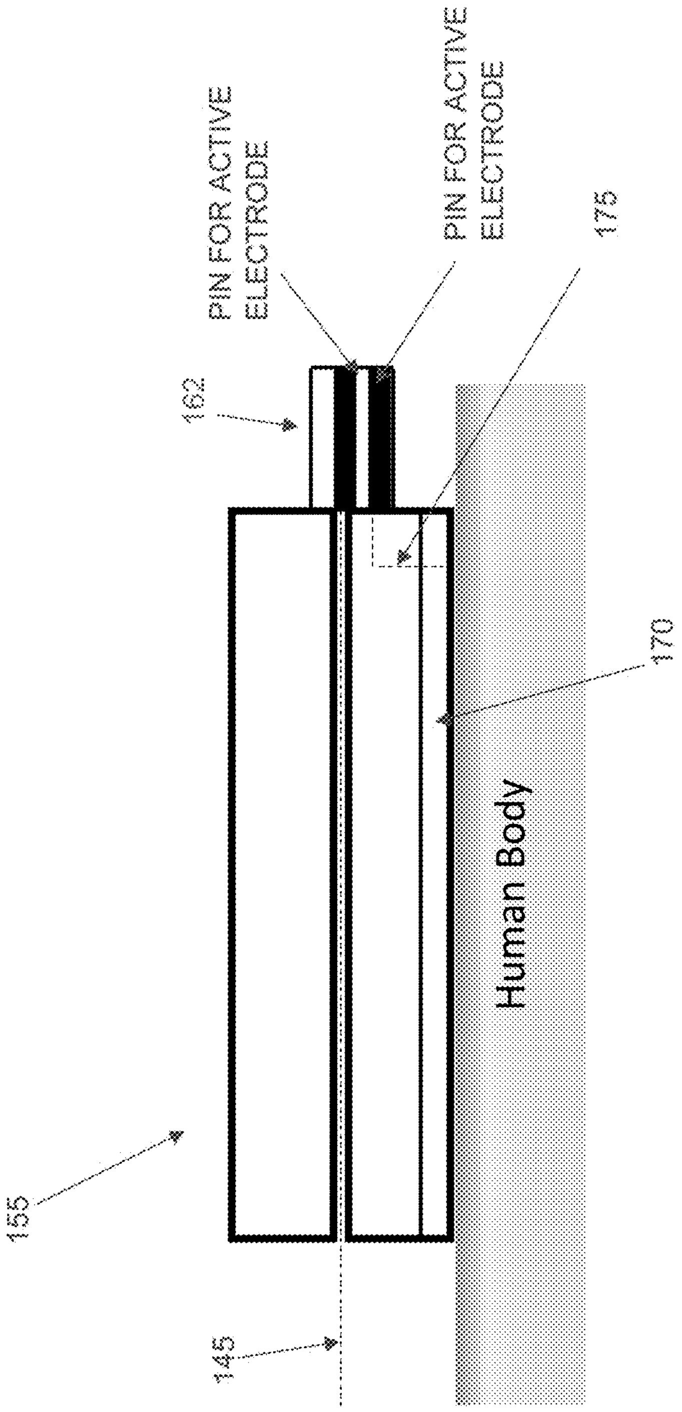

Additionally, while FIG. 7 depicts a novel electrode 100 in which non-conductive coating 120 has been applied to two different ends (e.g., regions) of conductive thread 105, it should be appreciated that, if desired, non-conductive coating 120 may be applied to only one end of the conductive thread. Additionally, if desired, non-conductive coating may be applied to more than one region of conductive thread 105, and the coated regions of conductive thread 105 may be of various lengths, including different lengths on each side of the uncoated, conductive region of conductive thread 105.

By way of example but not limitation, and still looking at FIG. 7, in one preferred form of the present invention, electrode 100 comprises a conductive thread 105 that is 6 cm in length extending between first and second sticky pads 110, 115, with a first region 125 comprising non-conductive coating 120 extending a length of 0.5 cm from first sticky pad 110 towards second sticky pad 115, and with a second region 130 comprising non-conductive coating 120 extending a length of 2.5 cm from the second sticky pad 115 towards first sticky pad 110, whereby to leave an exposed conductive region 135 having a length of 3 cm). In a preferred form of the present invention, non-conductive coating 120 comprises silicone.

It should be appreciated that there are various different materials that may be used for first and second sticky pads 110, 115. More particularly, first and second sticky pads 110, 115 may comprise any material that permits an adhesive surface on one side (i.e., to enable the electrode to be mounted to the skin of the test subject), and that is also able to electrically isolate the conductive thread(s) 105 from the skin of the test subject. In a preferred form of the invention, first and second sticky pads 110, 115 comprise a material comprising soft foam, rubber, soft plastic or some combination of those materials, however, other materials may be used which will be apparent to those of skill in the art in view of the present disclosure.

The use of novel electrode 100 provides at least two significant benefits when compared to prior art DTL electrodes.

Figure 5:
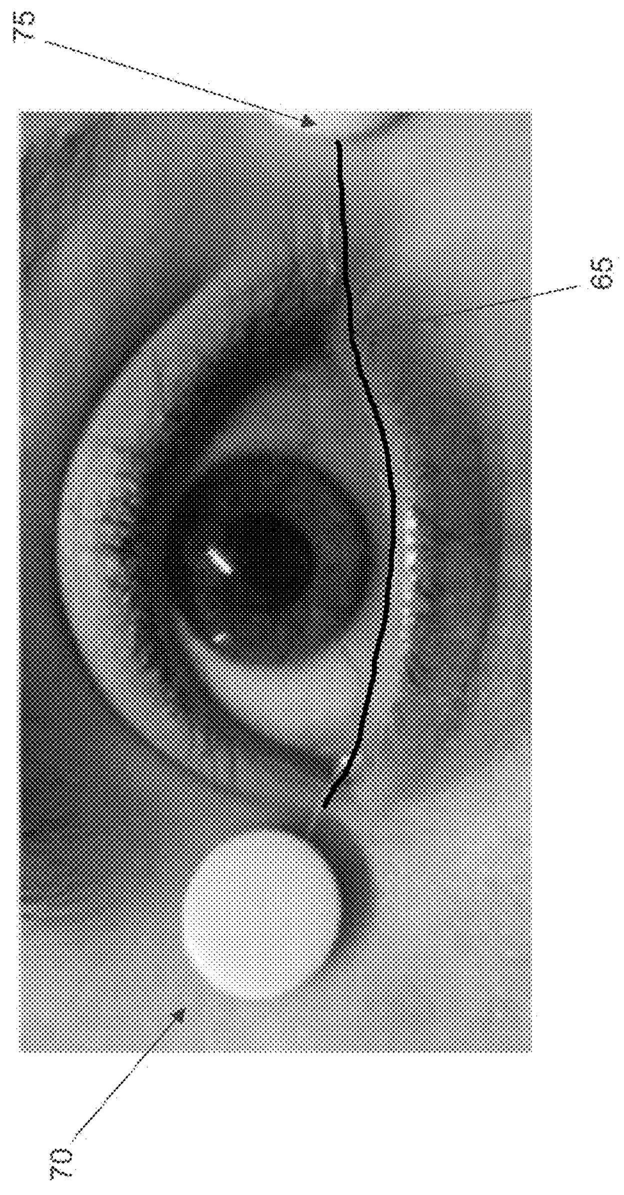
FIG. 5 is a schematic view showing typical positioning of a conductive thread of a prior art DTL electrode relative to the human eye.

First, and looking now at the prior art DTL electrode depicted in FIG. 5, it will be appreciated that, with prior art DTL electrodes, the conductive thread of the prior art DTL electrode contacts many portions of the body in addition to the cornea or the conjunctiva (i.e., the two areas of the eye for which the electrical potential to be measured by the electrode is of the greatest interest for performing ERG tests). These "undesirable" areas for electrical contact include facial skin on both sides of the eye as well as the caruncula, and a large width of the sclera.

In contrast, because the conductive thread 105 of novel electrode 100 of the present invention is coated with non-conductive coating 120 in the regions of conductive thread 105 that would come into contact with the areas of the skin that are "undesirable" for electrical contact (i.e., facial skin on both sides of the eye, the caruncula and large portions of the outer edges of the sclera), the "undesirable" areas of the skin that non-conductive coating 120 contacts are electrically isolated. Electrically isolating the "undesirable" areas of the skin, maximizes electrical contact between the conductive portion of conductive thread 105 and the lower portion of the cornea or the upper portion of the conjunctiva, near the center of the eye.

Thus, the novel electrode 100 of the present invention increases the measured electrical potential signal because it is in electrical contact with higher voltage potential portions of the eye, compared to prior art DTL electrodes. Furthermore, non-conductive coating 120 eliminates variability of the measured potential emanating from the skin around the eye, given that the area of conductive thread 105 is no longer electrically in contact with the skin around the eye (i.e., due to the insulation provided by non-conductive coating 120).

The second significant benefit of novel electrode 100 is that the regions of conductive thread 105 coated in non-conductive coating 120 act to stiffen conductive thread 105. This enhances the ability of the clinician/technician to position the conductive portion of conductive thread 105 in the same position on the eye of the test subject with greater repeatability, from test to test, and helps ensure that conductive region 135 of conductive thread 105 is positioned so as to contact the most advantageous region of the test subject's eye (e.g., location B shown in FIG. 6).

Figure 6:
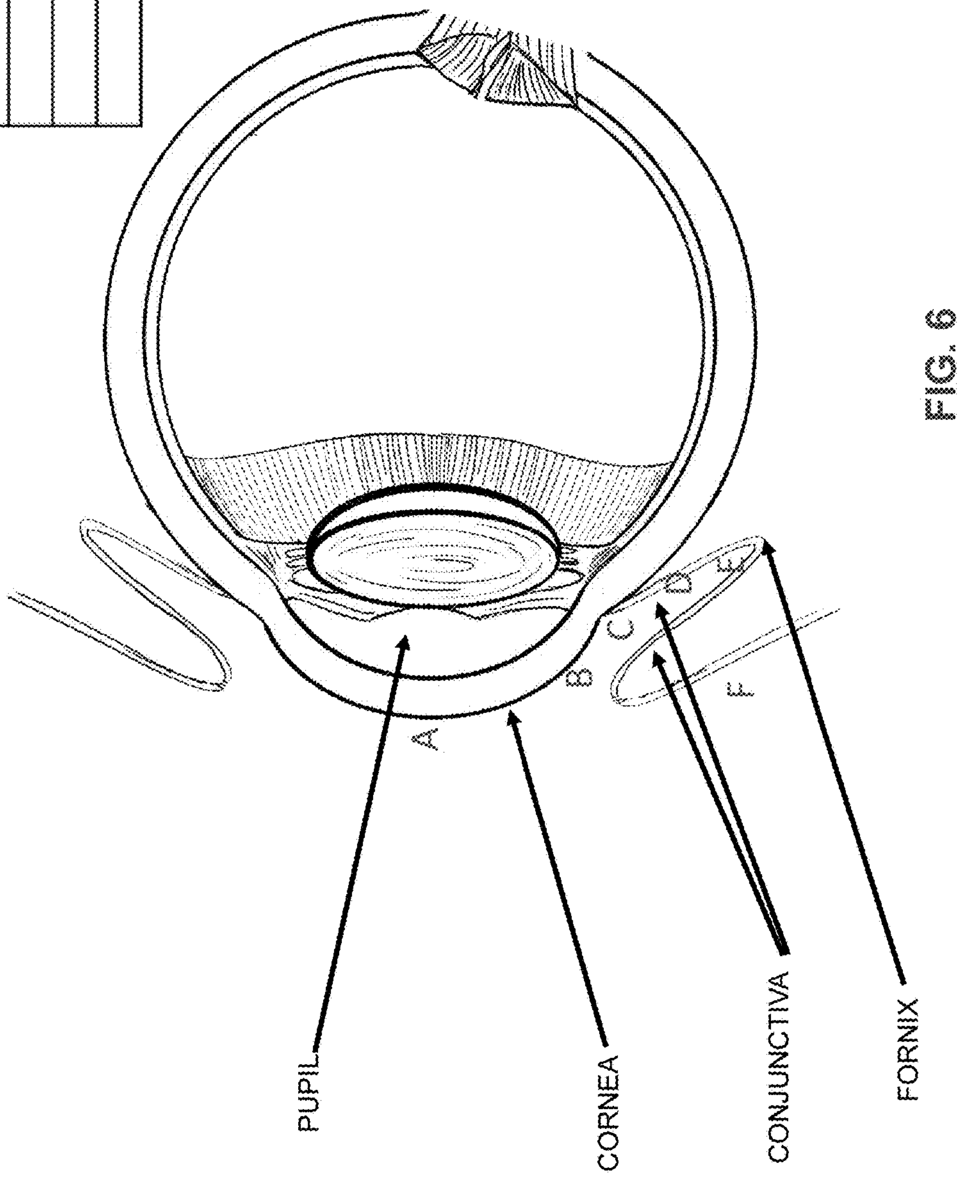
FIG. 6 is a schematic view of a human eye, illustrating the anatomy of the eye and the relative electrical potential that can be measured at different regions of the eye.

Looking again at FIG. 6, without the provision of non-conductive coating 120 on conductive thread 105 provided by novel electrode 100, the conductive region of conductive thread 105 may end up disposed in positions ranging from location B through location E and, as shown in the table of FIG. 6, certain positions result in a variability of 30-50% in the amplitude measured, even if all other factors are the same.

In tests of novel electrode 100 utilizing non-conductive coating 120 comprising silicone to cover first region 125 of conductive thread 105 for a length of 0.5 cm extending from first sticky pad 110 towards second sticky pad 115, and non-conductive coating 120 comprising silicone to cover second region 130 of conductive thread 105 for a length 2.5 cm extending from second sticky pad 115 toward first sticky pad 110, significant improvements in intersession repeatability and ERG signal amplitude were achieved. Benchmark testing was conducted that entailed over 70 full-field ERG tests using commercially available prior art DTL electrodes and over 80 tests using the novel DTL-style electrode 100 of the present invention. In each test, the electrode was replaced on the test subject after performing an ERG, thereby requiring a new electrode to be placed on the test subject's eye each time, creating an intersession test scenario. In each of the full-field ERG tests the a-wave (cone response), b-wave (bipolar cell response) and PhNR (retinal ganglion cell response) were measured. In each case, a well-trained clinician placed the electrodes (either the prior art DTL electrode or novel electrode 100 of the present invention) as close as they could to the optimal position. The tests showed increased amplitudes recorded using the novel electrode 100 of the present invention when compared to the amplitudes recorded using prior art DTL electrodes: a-wave of +17%, b-wave of +18% and PhNR of +16%. Most importantly the intersession repeatability (defined as 1 standard deviation divided by the average amplitude, of each set of tests) of the novel electrode 100 of the present invention compared to prior art DTL electrodes for the a-wave, b-wave and PhNR improved from 17%, 18%, and 17% to be 9%, 7% and 7%, respectively. These are very significant intersession repeatability improvements that open new clinical applications for ERG testing in general.

Second Novel Aspect of the Invention: Bipolar Electrode

A second novel aspect of the present invention is the provision and use of a novel DTL-style electrode which incorporates a reference electrode into the electrode, thereby forming a bipolar electrode. As discussed above, for each ERG measurement, two electrode measurements are required, i.e., an "active" electrode measurement and a "reference" electrode measurement. The difference between the measurement recorded by the "active" electrode and the measurement recorded by the "reference" electrode is reported as the ERG amplitude by the ERG system. Prior art DTL electrodes have only used one electrode (i.e., such prior art DTL electrodes are monopolar), with the conductive thread of the DTL electrode constituting the single electrode in contact with the body.

The present invention improves upon prior art DTL electrodes by incorporating a second electrode to serve as the reference electrode, thus creating a bipolar DTL-style electrode.

More particularly, and looking now at FIGS. 9, 9A, 10 and 10A, there is shown a novel bipolar electrode 140 formed in accordance with the present invention. Bipolar electrode 140 generally comprises a conductive thread 145, a first sticky pad 150 for mounting bipolar electrode 140 to the skin on one side of the eye of a test subject, and a second sticky pad 155 for mounting bipolar electrode 140 to the skin on the opposite side of the eye of the test subject. Sticky pads 150, 155 comprise a non-conductive material and, if desired, may comprise several layers for "sandwiching" and isolating conductive elements of bipolar electrode 140 from one another as will be apparent to one of skill in the art in view of the present disclosure. Conductive thread 145 may comprise a single conductive thread or, if desired, conductive thread 105 may comprise a bundle of conductive threads. An electrical cable and connector 160 (FIGS. 9 and 9A), or an electrical connector pin 162 (FIGS. 10 and 10A), extends from second sticky pad 155 and is in electrical connection with conductive thread 145, whereby to permit bipolar electrode 140 to be connected to an amplifier and/or controller and/or computer in a manner that will be apparent to those of skilled in the art in view of the present disclosure. If desired, electrical cable and connector 160 may comprise two, electrically-isolated electrical channels for conducting electrical signals separately from conductive thread 145 and a second, separate electrical contact serving as a reference electrode, which will hereinafter be discussed in further detail.

Second sticky pad 155 comprises a bottom surface 165 having a conductive element 170 applied thereto (or mounted thereto), whereby to serve as a reference electrode in contact with the test subject's skin. Conductive element 170 (serving as the "reference" electrode) is electrically isolated from the conductive path of conductive thread 145 by a layer of the non-conductive material of which second sticky pad 155 is comprised.

Alternatively, if desired, conductive element 170 (serving as the "reference" electrode) may be mounted to bottom surface 165 of second sticky pad 155 so as to protrude in a radial direction from bottom surface 165 of second sticky pad 155. More particularly, in this form of the invention, conductive element 170 generally comprises a small tab (not shown) protruding from second sticky pad 155 which contacts the test subject's skin and is electrically isolated from the conductive path of conductive thread 145 (serving as the "active" electrode). In all cases, given that the second sticky pad 155 is intended to mount at a location at or near the temple of the test subject, the incorporation of conductive element 170 into second sticky pad 155 positions the "reference" electrode at one of the optimal locations for a reference electrode to be located when performing an ERG test.

A conductive connector wire 175 extends from conductive element 170 through second sticky pad 155 to electrical cable connector 160, whereby to transmit electrical signals from conductive element 170 to a channel of electrical cable connector 160. Conductive wire 175 is electrically isolated from conductive thread 145 in a manner that will apparent to one of ordinary skill in the art in view of the present disclosure.

Compared to using a monopolar prior art DTL electrode requiring a separate reference electrode, the advantages of the novel bipolar electrode 140 of the present invention include improved performance, ease of use and lower cost. Additionally, because novel bipolar electrode 140 incorporates the "reference" electrode into an element of bipolar electrode 140 (i.e., into second sticky pad 155 of bipolar electrode 140) it is much easier for the technician to position the reference electrode (i.e., conductive element 170) on the test subject in the same place over many tests, thus improving electrode performance and repeatability of the ERG test. And, by providing the "active" electrode (i.e., conductive thread 145) and the "reference" electrode (i.e., conductive element 170) in a single bipolar electrode (i.e., bipolar electrode 140), it takes the technician setting up a test subject for an ERG test less time to do so inasmuch as bipolar electrode 140 takes the same amount of time to apply to a test subject as a prior art monopolar DTL electrode, and no separate reference electrode element is required to be positioned on the test subject. Finally, due to its integrated design, novel bipolar electrode 140 is more cost effective to manufacture than the two separate electrodes previously required by prior art ERG systems (e.g., a monopolar DTL electrode and a separate reference electrode).

It should also be appreciated that in most ERG recordings a ground electrode is also utilized. If desired, the ground electrode can also be integrated into second sticky pad 155 of novel bipolar electrode 140 in a manner similar to the manner in which conductive element 170 is mounted to second sticky pad 155 to serve as the "reference" electrode (in which case, second sticky pad 155 would further comprise a second conductive connector wire for electrically connecting the ground electrode to electrical cable and connector 160 (or pin 162), and electrical cable and connector 160 would comprise an additional channel for carrying the electrical signal of the ground electrode). Thus, where second sticky pad 155 further comprises a ground electrode, the ground electrode would include a conductive element that would be electrically isolated from conductive element 170 (i.e., the "reference" electrode), while remaining in contact with the skin of the test subject.

Finally, it should be appreciated that, if desired, conductive thread 145 of bipolar electrode 140 may comprise the aforementioned non-conductive coating 120 over one or more regions of the conductive thread 145, whereby to provide the benefits associated with novel DTL-style electrode 100 discussed above.

Third Novel Aspect of the Invention: Novel Sticky Pad Shapes

A third novel aspect of the present invention is the provision and use of novel sticky pads comprising novel shapes and/or materials incorporated as a part of, or next to, the sticky pads.

Figure 11:
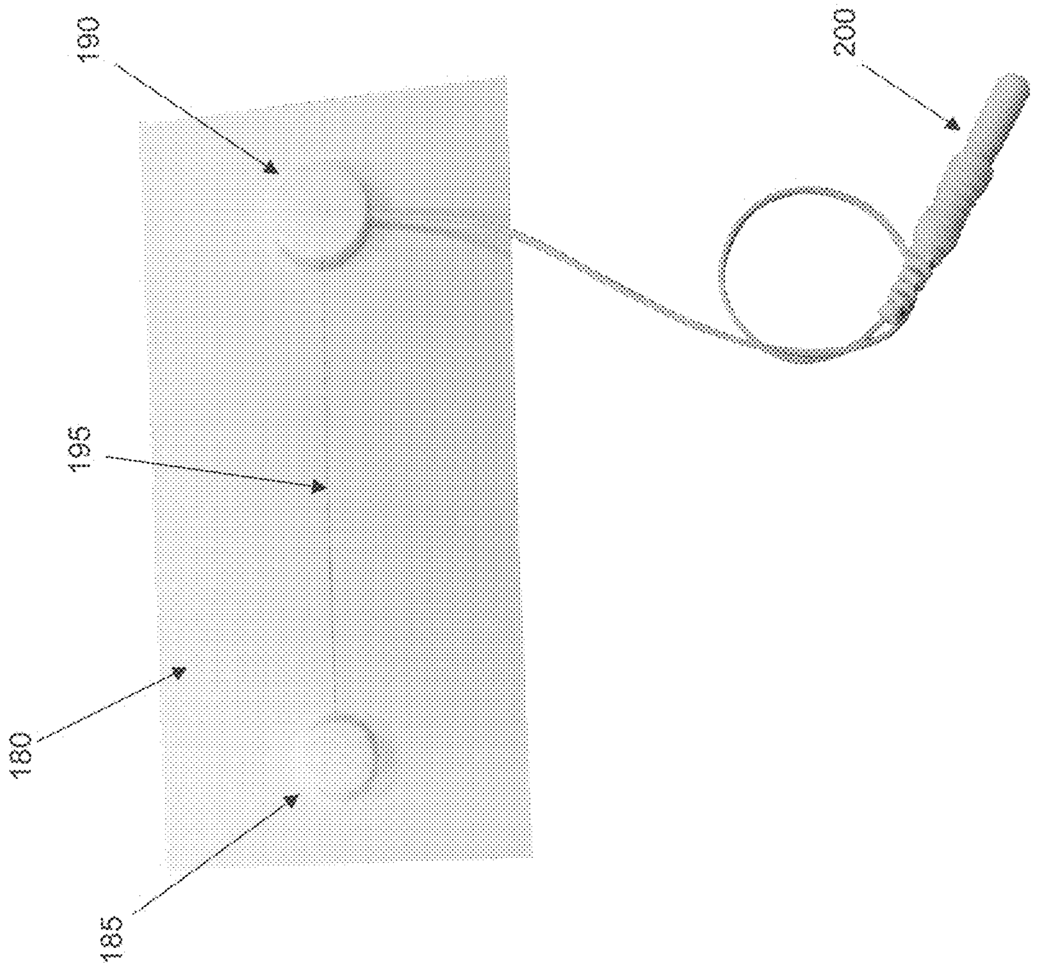
FIGS. 11 and 12 are schematic views of a prior art DTL electrode illustrating round sticky pads used in connection with the same.
Figure 12:

More particularly, all prior art DTL electrodes currently in use utilize round sticky pads. See, for example, FIGS. 11 and 12, which show an exemplary prior art DTL electrode 180 comprising a first round sticky pad 185, a second round sticky pad 190, a conductive thread 195 extending therebetween, and an electrical cable connector 200 in electrical connection with conductive thread 195. As discussed above, it is preferably to provide sticky pads which electrically isolate the conductive thread (i.e., conductive thread 195 of an exemplary prior art DTL electrode) from skin around the eye, as well as to provide additional stiffness on, under (or both) to the conductive thread next to the eye.

The present invention recognizes that sticky pads comprising non-circular shapes offer the benefit of electrically isolating the conductive thread of the active electrode (i.e., conductive thread 105 and 145 of the novel electrodes of the present invention, or conductive thread 195 of a prior art DTL electrode) from skin directly next to the eye, while also providing additional stiffness of the thread just before it contacts the eye, whereby to help properly position the conductive thread across the eye.

Figure 13:
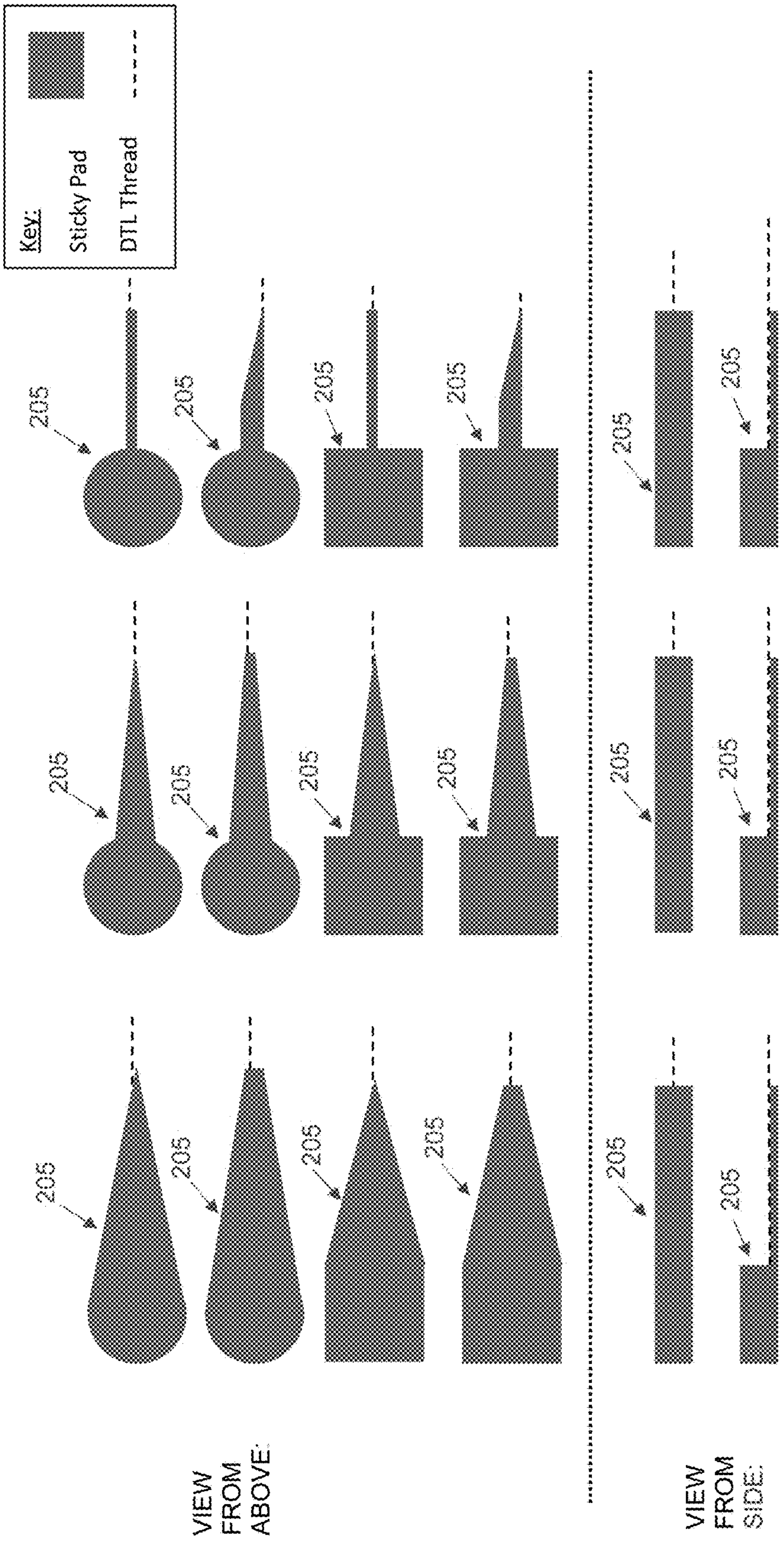
FIG. 13 is a schematic view illustrating novel sticky pads formed in accordance with the present invention.

More particularly, FIG. 13 shows novel sticky pads 205 comprising novel shapes formed in accordance with the present invention. It will be appreciated that novel sticky pads 205 may be used with novel DTL-style electrode 100, novel bipolar electrode 140, or prior art DTL electrode 180 in lieu of the first and second sticky pads of those electrodes. Sticky pads 205 can be used for the sticky pad on each side of the eye of the test subject, or for the sticky pad on only one side of the eye of the test subject. In each case, the widest portion of sticky pad 205 is used primarily to attach the sticky pad to the test subject's skin (e.g., near the temple of the test subject), and the narrower portion of sticky pad 205 is used to isolate the conductive thread (serving as the "active" electrode) from the skin of the test subject, and to guide the thread into the corner of the eye of the test subject. Various aspect ratios of these shapes are used to be accommodate the shape of a test subject's face in the region of the eye. Typically, the sticky pad to be mounted to the test subject nearest to the test subject's nose is smaller (and not as wide as) the sticky pad mounted to the temple side of the eye of the test subject. A wide array of sticky pads 205 comprising various shapes are shown in FIG. 13, where the view from above and from the side of sticky pads 205 show how the geometry of the sticky pads 205 may be configured such that (i) the shape of the sticky pad viewed from the top surface varies, and/or (ii) the depth of a particular region of the sticky pad viewed from the side varies. Any combination of the shapes/geometries depicted in FIG. 13 may be used to form novel sticky pads 205. Additionally, sticky pads 205 may comprise one or more materials selected from the group consisting of foam, plastic, rubber, fabric, and other materials (or combination of materials). A thin layer of adhesive (not shown) is preferably applied to a bottom surface of each sticky pad 205 so as to cover the full underside of the sticky pad, or just a portion of it. Reference and potential ground electrode pads may be incorporated as well, as will be apparent to one of ordinary skill in the art in view of the present disclosure.

Modifications

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An apparatus for use in performing electroretinography on a test subject, the apparatus comprising:

a plurality of flexible threads each coated with an electrically conductive material so as to form a plurality of flexible electrically conductive threads, the plurality of flexible electrically conductive threads each comprising a first end, a second end and a central portion extending between the first end and the second end;

wherein the first end of the plurality of flexible electrically conductive threads comprises an electrically non-conductive coating which forms a first bundled thread at the first end of the plurality of flexible electrically conductive threads;

wherein the second end of the plurality of flexible electrically conductive threads comprises an electrically non-conductive coating which forms a second bundled thread at the second end of the plurality of flexible electrically conductive threads;

wherein the first bundled thread is configured to mount to a first sticky pad, wherein the first sticky pad is configured to mount to skin on one side of an eye of the test subject such that the first bundled thread extends along a first portion of the eye of the test subject to electrically isolate the first portion of the eye of the test subject, the second bundled thread is configured to mount to a second sticky pad, wherein the second sticky pad is configured to mount to skin on the opposite side of the eye of the test subject such that the second bundled thread extends along a second portion of the eye of the test subject to electrically isolate the second portion of the eye of the test subject and the plurality of flexible electrically conductive threads of the central portion are configured to contact a surface film at a third portion of the eye of the test subject to measure an electrical response at only the third portion of the eye of the test subject;

wherein the first sticky pad and the second sticky pad each comprise a top surface and a bottom surface; and wherein at least one of a reference electrode and a ground electrode is mounted to the bottom surface of one of the first sticky pad and the second sticky pad.

2. The apparatus according to claim 1, wherein the second sticky pad comprises an electrical cable connector electrically connected to the second bundled thread, and further wherein the electrical cable connector is configured to receive a lead connected to external electronics.

3. The apparatus according to claim 2 wherein the external electronics comprise at least one selected from the group consisting of an amplifier, a controller and a computer.

4. The apparatus according to claim 1 wherein the electrically non-conductive coating comprises a non-conductive material applied as a coating that is between 1 and 20 microns in thickness.

5. The apparatus according to claim 1 wherein the electrically non-conductive coating comprises silicone.

6. The apparatus according to claim 1 wherein the at least one electrically conductive material comprises silver.

7. The apparatus according to claim 1 wherein the electrically non-conductive coating is applied to 0.5 cm of the first end to form the first bundled thread and 2.5 cm of the second end to form the second bundled thread, and further wherein the central portion has a length of 3 cm.

8. The apparatus according to claim 1 wherein the first sticky pad and the second sticky pad comprise an adhesive for facilitating mounting to the skin.

9. The apparatus according to claim 1 wherein the first sticky pad and the second sticky pad comprise at least one material selected from the group consisting of soft foam, rubber, soft plastic or some combination thereof.

10. The apparatus according to claim 1 wherein the electrically non-conductive coating is configured to stiffen the plurality of flexible electrically conductive threads, whereby to facilitate positioning of the plurality of flexible electrically conductive threads relative to the eye.

11. A method for performing electroretinography on a test patient, the method comprising:

providing an apparatus comprising:

a plurality of flexible threads each coated with an electrically conductive material so as to form a plurality of flexible electrically conductive threads, the plurality of flexible electrically conductive threads each comprising a first end, a second end and a central portion extending between the first end and the second end;

wherein the first end of the plurality of flexible electrically conductive threads comprises an electrically non-conductive coating which forms a first bundled thread at the first end of the plurality of flexible electrically conductive threads;

wherein the second end of the plurality of flexible electrically conductive threads comprises an electrically non-conductive coating which forms a second bundled thread at the second end of the plurality of flexible electrically conductive threads;

mounting the first bundled thread to a first sticky pad and mounting the first sticky pad to the skin on one side of an eye of the test subject such that the first bundled thread extends along a first portion of the eye of the test subject to electrically isolate the first portion of the eye of the test subject, and mounting the second bundled thread to a second sticky pad and mounting the second sticky pad to the skin on the opposite side of the eye of the test subject such that the second bundled thread extends along a second portion of the eye of the test subject to electrically isolate the second portion of the eye of the test subject, and such that the plurality of flexible electrically conductive threads of the central portion are in electrical contact with a third portion of the eye of the test subject;

wherein the first sticky pad and the second sticky pad each comprise a top surface and a bottom surface; and wherein at least one of a reference electrode and a ground electrode is mounted to the bottom surface of one of the first sticky pad and the second sticky pad; and measuring an electrical response at only the third portion of the eye of the test subject.

12. The apparatus according to claim 2 wherein the electrical cable connector comprises a first channel and a second channel, wherein the first channel is electrically isolated from the second channel, wherein the central portion is electrically connected to the first channel, and wherein the conductive element is electrically connected to the second channel.

13. The apparatus according to claim 1 wherein at least one of the first sticky pad and the second sticky pad is defined by a plane having a non-circular perimeter;

wherein the non-circular perimeter comprises a wide portion and a narrow portion, wherein the wide portion is configured to be positioned adjacent to the temple of the test subject, and the narrow portion is configured to guide the central portion toward the eye of the test subject.

14. The apparatus according to claim 1 wherein the distance between the top surface of the sticky pad and the bottom surface of the sticky pad differs at different locations of the plane defined by the top surface of the sticky pad, such that the sticky pad comprises regions having varying widths.

15. An apparatus for use in performing electroretinography on a test subject, the apparatus comprising:

a plurality of flexible threads each coated with an electrically conductive material so as to form a plurality of flexible electrically conductive threads, the plurality of flexible electrically conductive threads each comprising a first end, a second end and a central portion extending between the first end and the second end;

wherein the first end of the plurality of flexible electrically conductive threads comprises an electrically non-conductive coating which forms a first bundled thread at the first end of the plurality of flexible electrically conductive threads;

wherein the second end of the plurality of flexible electrically conductive threads comprises an electrically non-conductive coating which forms a second bundled thread at the second end of the plurality of flexible electrically conductive threads;

wherein the first bundled thread is configured to mount to a first sticky pad, wherein the first sticky pad is configured to mount to skin on one side of an eye of the test subject such that the first bundled thread extends along a first portion of the eye of the test subject to electrically isolate the first portion of the eye of the test subject, the second bundled thread is configured to mount to a second sticky pad, wherein the second sticky pad is configured to mount to skin on the opposite side of the eye of the test subject such that the second bundled thread extends along a second portion of the eye of the test subject to electrically isolate the second portion of the eye of the test subject and the plurality of flexible electrically conductive threads of the central portion are configured to contact a surface film at a third portion of the eye of the test subject to measure an electrical response at only the third portion of the eye of the test subject;

wherein the electrically non-conductive coating is applied to 0.5 cm of the first end to form the first bundled thread and 2.5 cm of the second end to form the second bundled thread, and further wherein the central portion has a length of 3 cm.

16. The apparatus according to claim 15 wherein the first sticky pad and the second sticky pad are electrically isolated from the skin.

17. The apparatus according to claim 15 wherein the electrically non-conductive coating comprises a non-conductive material applied as a coating that is between 1 and 20 microns in thickness.

18. The apparatus according to claim 15 wherein the electrically non-conductive coating comprises silicone.

19. The apparatus according to claim 15 wherein the at least one electrically conductive material comprises silver.

20. The apparatus according to claim 15 wherein the first sticky pad and the second sticky pad comprise an adhesive for facilitating mounting to the skin.

21. The apparatus according to claim 15 wherein the first sticky pad and the second sticky pad comprise at least one material selected from the group consisting of soft foam, rubber, soft plastic or some combination thereof.

22. The apparatus according to claim 15 wherein the electrically non-conductive coating is configured to stiffen the plurality of flexible electrically conductive threads, whereby to facilitate positioning of the plurality of flexible electrically conductive threads relative to the eye.

23. The apparatus according to claim 15 wherein the second sticky pad comprises a conductive element mounted to the bottom surface, whereby to make electrical contact with the skin when the second sticky pad is mounted to the skin.

24. The apparatus according to claim 23 further comprising an electrical cable connector mounted to the second sticky pad, the electrical cable connector being in electrical connection with the central portion and the conductive element, and the electrical cable connector being configured to electrically connect to a lead connected to external electronics.

25. The apparatus according to claim 24 wherein the external electronics comprise at least one selected from the group consisting of an amplifier, a controller and a computer.

26. The apparatus according to claim 24 wherein the electrical cable connector comprises a first channel and a second channel, wherein the first channel is electrically isolated from the second channel, wherein the central portion is electrically connected to the first channel, and wherein the conductive element is electrically connected to the second channel.

27. The apparatus according to claim 23 wherein the plurality of flexible electrically conductive threads of the central portion are configured to contact the surface film of an eye, whereby to serve as an active electrode for performing electroretinography, and further wherein the conductive element is configured to contact the skin, whereby to serve as a reference electrode for performing electroretinography.

28. The apparatus according to claim 15 wherein at least one of the first stick pad and the second sticky pad is defined by a plane having a non-circular perimeter;

wherein the non-circular perimeter comprises a wide portion and a narrow portion, wherein the wide portion is configured to be positioned adjacent to the temple of the test subject, and the narrow portion is configured to guide the central portion toward the eye of the test subject.

29. The apparatus according to claim 15 wherein the distance between the top surface of the sticky pad and the bottom surface of the sticky pad differs at different locations of the plane defined by the top surface of the sticky pad, such that the sticky pad comprises regions having varying widths.

30. The apparatus according to claim 15 wherein at least one of a reference electrode and a ground electrode is mounted to the bottom surface of one of the first sticky pad and the second sticky pad.

31. A method for performing electroretinography on a test patient, the method comprising:

providing an apparatus comprising:

a plurality of flexible threads each coated with an electrically conductive material so as to form a plurality of flexible electrically conductive threads, the plurality of flexible electrically conductive threads each comprising a first end, a second end and a central portion extending between the first end and the second end;

wherein the first end of the plurality of flexible electrically conductive threads comprises an electrically non-conductive coating which forms a first bundled thread at the first end of the plurality of flexible electrically conductive threads;

wherein the second end of the plurality of flexible electrically conductive threads comprises an electrically non-conductive coating which forms a second bundled thread at the second end of the plurality of flexible electrically conductive threads;

wherein the electrically non-conductive coating is applied to 0.5 cm of the first end to form the first bundled thread and 2.5 cm of the second end to form the second bundled thread, and further wherein the central portion has a length of 3 cm;

mounting the first bundled thread to a first sticky pad and mounting the first sticky pad to the skin on one side of an eye of the test subject such that the first bundled thread extends along a first portion of the eye of the test subject to electrically isolate the first portion of the eye of the test subject, and mounting the second bundled thread to a second sticky pad and mounting the second sticky pad to the skin on the opposite side of the eye of the test subject such that the second bundled thread extends along a second portion of the eye of the test subject to electrically isolate the second portion of the eye of the test subject, and such that the plurality of flexible electrically conductive threads of the central portion are in electrical contact with a third portion of the eye of the test subject; and measuring an electrical response at only the third portion of the eye of the test subject.

* * * * *